US010302629B2

(12) United States Patent
Carrier

(10) Patent No.: US 10,302,629 B2
(45) Date of Patent: May 28, 2019

(54) COMPOSITIONS AND METHODS FOR TREATING CANCER BY RATIONAL TARGETING OF PROTEIN TRANSLATION

(71) Applicant: France Carrier, Highland, MD (US)

(72) Inventor: France Carrier, Highland, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/084,459

(22) Filed: Mar. 29, 2016

(65) Prior Publication Data
US 2016/0289311 A1  Oct. 6, 2016

Related U.S. Application Data

(60) Provisional application No. 62/139,860, filed on Mar. 30, 2015.

(51) Int. Cl.
*C12N 15/113* (2010.01)
*G01N 33/50* (2006.01)
*C07K 16/00* (2006.01)

(52) U.S. Cl.
CPC .......... *G01N 33/5011* (2013.01); *C07K 16/00* (2013.01); *C12N 15/113* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos | |
| 4,501,728 A | 2/1985 | Geho | |
| 4,837,028 A | 6/1989 | Allen | |
| 4,920,016 A | 4/1990 | Allen | |
| 5,019,369 A | 5/1991 | Presant | |
| 2005/0251872 A1* | 11/2005 | Bear | A01K 67/0275 800/8 |
| 2011/0313233 A1* | 12/2011 | Getzenberg | A61K 31/282 600/3 |

OTHER PUBLICATIONS

Fornace et al., DNA damage-inducible transcripts in mammalian cells, Proc Natl Acad Sci USA, 85:8800-8804 (1988).
Sheikh et al., Identification of Several Human Homologs of Hamster DNA Damage-inducible Transcripts, J Biol Chem, 272:26720-26726 (1997).
Nishiyama et al., Cloning and characterization of human CIRP (cold-inducible RNA binding protein) cDNA and chromosomal assignment of the gene, Gene, 204:115-120 (1997).
Al-Fageeh et at., Cold-inducible RNA binding protein (CIRP) expression is modulated by alternative mRNAs, RNA, 15:1164-1176 (2009).
Yang et al., The UV-inducible RNA-binding Protein A18 (A18 hnRNP) Plays a Protective Role in the Genotoxic Stress Response, J Biol Chem, 276:47277-47284 (2001).
Yang et al., Functional Significance fora Heterogenous Ribonucleoprotein A18 Signature RNA Motif in the 3'-Untranslated Region of Ataxia Telangiectasia Mutated and Rad3-related (ATR) Transcript, J Biol Chem, 285:8887-8893 (2010).
Yang et al., Post-transcriptional regulation of thioredoxin by the stress inducible heterogenous ribonucleoprotein A18J, Nucleic Acid Research, 34:1224-1236 (2006).
Artero-Castro et al., Cold-Inducible RNA-Binding Protein Bypasses Replicative Senescence in Primary Cells through Extracellular Signal-Regulated Kinase 1 and 2 Activation, Mol Cell Biol, 29:1855-1868 (2009).
Harris et al., Hypoxia—A Key Regulatory Factor in Tumour Growth, Nat Rev Cancer, 2:38-47 (2002).
Wellmann et al., Oxygen-regulated expression of the RNA-binding proteins RBM3 and CIRP by a HIF-1-independent mechanism, J Cell Sci, 117:1785-1794 (2004).
Pamboukian R CF., hnRNP A18: A New Pathway to Regulate Protein Translation in Cancer Cells, Molecular and Cellular Pharmacology, 4:41-48 (2012).
Brummelkamp et al., A System for Stable Expression of Short Interfering RNAs in Mammalian Cells, Science, 296:550-553 (2002).
Lee et al., Expression of small interfering RNAs targeted against HIV-1 rev transcripts in human cells, Nature Biotechnol, 20:500-505 (2002).
Miyagishi et al., U6 promoter—driven siRNAs with four uridine 3' overhangs efficiently suppress targeted gene expression in mammalian cells, Nature Biotechnol, 20:497-500 (2002).
Paddison et al., Short hairpin RNAs (shRNAs) induce sequence-specific silencing in mammalian cells, Genes & Dev,16:948-958 (2002).
Paul et al., Effective expression of small interfering RNA in human cells, Nature Biotechnol, 20:505-508 (2002).
Sui et al., A DNA vector-based RNAi technology to suppress gene expression in mammalian cells, Proc. Natl. Acad. Sci. USA, 99:5515-5520 (2002).
Yu et al., RNA interference by expression of short-interfering RNAs and hairpin RNAs in mammalian cells, Proc. Natl. Acad. Sci. USA, 99:6047-6052 (2002).

(Continued)

Primary Examiner — J. E. Angell
(74) Attorney, Agent, or Firm — Nevrivy Patent Law Group P.L.L.C.

(57) ABSTRACT

The present invention is drawn to therapeutics which can target hnRNP A18, a regulator of protein translation in cancer cells. The invention provides a method of treating cancer in a subject comprising administering to the subject a therapeutically effective amount of a composition that decreases the level and/or activity of heterogenous ribonucleoprotein A18 (hnRNP A18). The composition can comprise a nucleic acid molecule that binds to at least a portion of a nucleotide sequence coding for hnRNP A18. The invention also provides a composition for treating cancer comprising a nucleic acid or antibody that is capable of decreasing the level and/or activity of hnRNP A18 and a pharmaceutically acceptable carrier. The invention also provides methods of screening for an anti-cancer compound.

15 Claims, 12 Drawing Sheets
Specification includes a Sequence Listing.

(56) References Cited

OTHER PUBLICATIONS

Iyer et al., The Automated Synthesis of Sulfur-Containing Oligodeoxyribonucleotides Using 3H-1,2-Benzodithiol-3-one 1,1-Dioxide as a Sulfur-Transfer Reagent, J. Org. Chem., 55:4693-4698 (1990).
Iyer et al., 3H-1,2-Benzodithiole-3-one 1,1-Dioxide as an Improved Sulfurizing Reagent in the Solid-Phase Synthesis of Oligodeoxyribonucleide Phosphorothioates, J. Am. Chem. Soc., 112:1253-1254 (1990).
Dornburg, Reticuloendotheliosis viruses and derived vectors, Gene Therap., 2: 301-310 (1995).
Jewell, Gene Therapy, BMJ, 298:691-693 (1989).
Miller, Retrovirus Packaging Cells, Hum Gene Therap,1:5-14 (1990).
Anderson, Human gene therapy, Nature, 392:25-30 (1998).
Kanasty et al., Delivery materials for siRNA therapeutics, Nature Materials, 12:967-977 (2013).
Szoka et al., Comparative Properties and Methods of Preparation of Lipid Vesicles (Liposomes), Ann. Rev. Biophys. Bioeng., 9:467 (1980).
Gabizon et al., Liposome formulations with prolonged circulation time in blood and enhanced uptake by tumors, P.N.A.S. USA, 18: 6949-53 (1988).
Tenenbaum et al., Ribonomics: identifying mRNA subsets in mRNP complexes using antibodies to RNA-binding proteins and genomic arrays, Methods, 26:191-198 (2002).
Dewhirst et al., Cycling hypoxia and free radicals regulate angiogenesis and radiotherapy response, Nat Rev Cancer, 8:425-437 (2008).
Pamboukian et al., hnRNP A18: A New Pathway to Regulate Protein Translation in Cancer Cells, Mol Cell Pharmacol, 4:41-48 (2012).

\* cited by examiner

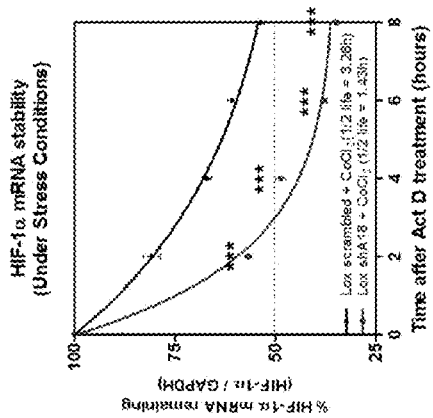
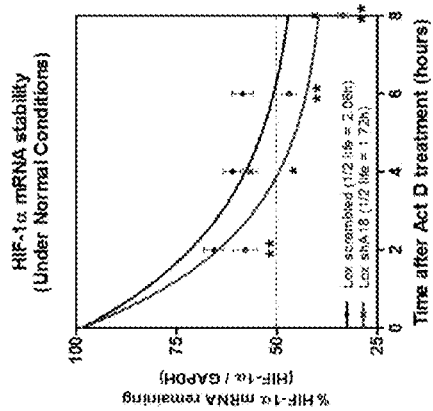
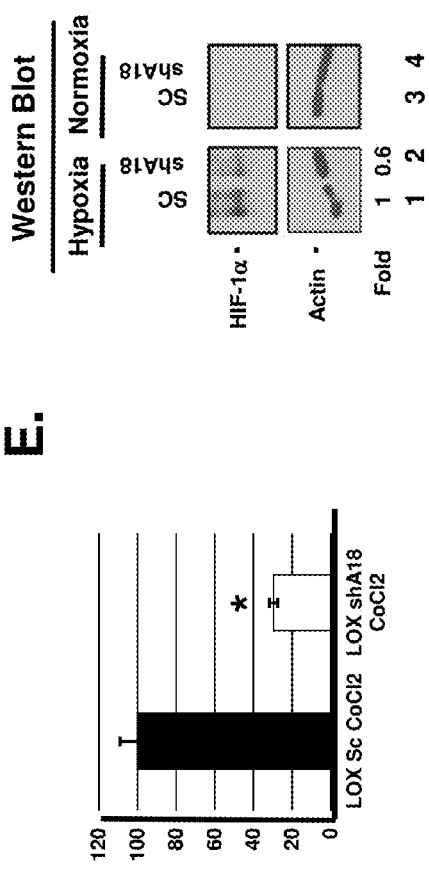
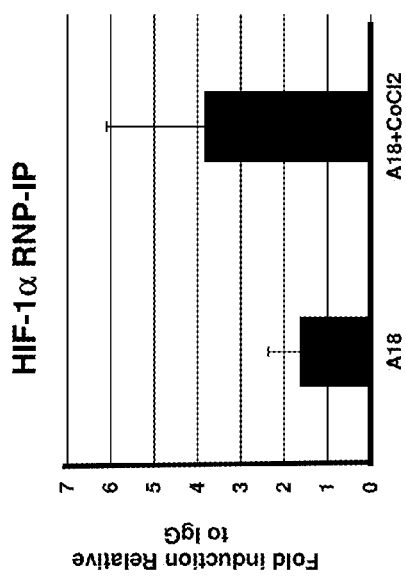
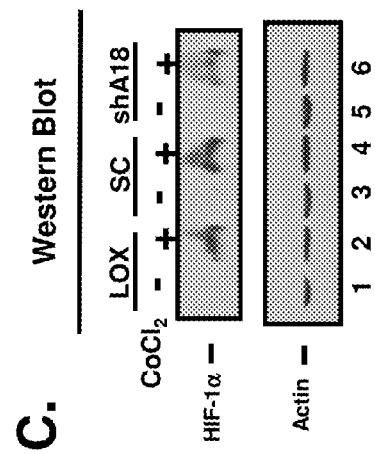
FIG. 4

FIG. 12

| Target | Sequence Alignment | Region | Accession | |
|---|---|---|---|---|
| TRX | taaaact:gtaatt:gttttaattt-a:aaaaatataaaatatgaaga: | (560-606) | NM_003329 | SEQ ID NO:13 |
| ATR | tccatata:gtgaaattgaattatgt:aaaagaatatgttaataatctta: | (8045-8092) | NM_001184 | SEQ ID NO:14 |
| EIF4G3 | actct--:gaaatc:ttagagca-a:tttaaggcttgtaaatac-a: | (5708-5750) | NM_003760 | SEQ ID NO:15 |
| EIF5A | cccaggg:gcgg-t:gtgcagc-a:gtgatcctctgaacctgcaga: | (708-753) | NM_001970 | SEQ ID NO:16 |
| EIF4E-BP2 | tttag--:gtggt:attgattc-a:gcagttctcatattctgttta: | (3691-3735) | NM_004096 | SEQ ID NO:17 |
| EEF1A1 | cagaac-:gtttgt:caattggcca:ttaagtttagtagtaaaaga: | (1507-1553) | NM_001402 | SEQ ID NO:18 |
| EEF1E1 | tgtctag-:gtgt:ctcatcaaga-a:cagactatactaattccca: | (550-595) | NM_004280 | SEQ ID NO:19 |
| RPA | cccaggg:ggga:tcttgaggagtta:caaataagcttgttaca: | (1383-1427) | NM_002946 | SEQ ID NO:20 |
| EIF3H | gaactct:gaag:cacacc----agggcaactcttggaagaat-a: | (1117-1158) | NM_003756 | SEQ ID NO:21 |
| EIF4E-BP1 | aggttga:gtgctt:gggaa---a:gctcccctcccctccttcccca: | (778-820) | NM_004095 | SEQ ID NO:22 |

COMPOSITIONS AND METHODS FOR TREATING CANCER BY RATIONAL TARGETING OF PROTEIN TRANSLATION

CROSS-REFERENCE TO RELATED APPLICATIONS

This application claims the benefit of U.S. Provisional Appl. No. 62/139,860, filed Mar. 30, 2015. The content of the aforementioned application is relied upon and is incorporated by reference in its entirety.

STATEMENT OF FEDERALLY SPONSORED RESEARCH AND DEVELOPMENT

This invention was made with government support under Grant Number CA177981 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 5,541 Byte ASCII (Text) file named "Sequences_ST25_r.txt," created on Dec. 20, 2017.

FIELD OF THE INVENTION

The field of the invention generally relates to the fields of medicine, molecular biology and cancer therapeutics.

BACKGROUND hnRNP A18 is a RNA-binding protein that was first identified as a UV-inducible transcript in CHO cells more than two decades ago (Fornace et al., Proc Natl Acad Sci USA. 1988; 85(23):8800-8804). Since then, the hnRNP A18 protein has been characterized in human cells (Sheikh et al, J Biol Chem. 1997; 272(42):26720-26726) and in mouse following exposure to mild cold shock. hnRNP A18 is thus also known as CIRP for Cold Inducible RNA Binding Protein (Nishiyama et al. Gene. 1997; 204(1-2):115-120). Three hnRNP A18/CIRP mRNA transcripts, differing mainly in the size of their 5' UTRs, have been described (Al-Fageeh M B and Smales C M., RNA. 2009; 15(6):1164-1176). The one we refer to as hnRNP A18 has the shortest 5'UTR and is expressed at 37° C. The two other transcripts are expressed at 32° C., harbor larger 5'UTRs and have shown internal ribosome entry segment (IRES)-like activity. hnRNP A18 is predominantly a nuclear protein but translocates to the cytoplasm in response to cellular stresses such as UV or hypoxia (Yang C and Carrier F., J Biol Chem. 2001; 276(50):47277-47284; Yang et al., J Biol Chem. 2010; 285(12):8887-8893). It is now becoming apparent that hnRNP A18 up-regulation is associated with a large number of solid tumors. In fact, immunohistochemistry staining of a variety of tumors from 193 patients indicate that hnRNP A18 is upregulated in about 30% of human tumors as compared to normal tissue from the same patients (Artero-Castro et al., Mol Cell Biol. 2009; 29(7):1855-1868). However, correlation with tumor grades or its potential tumor promoting activity in in vivo models has not been investigated so far.

Although a predominantly nuclear protein, hnRNP A18 has been located in the cytosol of several tumor cells (Artero-Castro et al., Mol Cell Biol. 2009; 29(7):1855-1868). This observation is consistent with the fact that most solid tumors develop hypoxic regions, mainly in the central core of the tumor, and that hnRNP A18 translocates to the cytosol in response to hypoxia (Harris A L., Nat Rev Cancer. 2002; 2(1):38-47; Wellmann et al., J Cell Sci. 2004; 117(Pt 9):1785-1794; Yang et al., J Biol Chem. 2010; 285(12):8887-8893). Earlier studies have revealed that hnRNP A18 translocation to the cytosol is mediated, in part, by the hypoxia inducible GSK-3βkinase and CK2 (Yang et al., Nucleic Acids Res. 2006; 34(4):1224-1236; Yang et al., J Biol Chem. 2010; 285(12):8887-8893). GSK-3βalso increases hnRNP A18 RNA binding activity and both, hnRNP A18 RNA binding domain and the RGG domain are required for maximal hnRNP A18 RNA binding activity (Yang et al., Nucleic Acids Res. 2006; 34(4):1224-1236). In the cytosol, hnRNP A18 binds to a specific 51 nucleotide RNA signature motif present in the 3'UTR of targeted transcripts and increases their translation by interacting with eukaryotic initiation factor 4G (eIF4G), a component of the general translation cap-binding complex eIF4F, on polysomes (Pamboukian R C F., Molecular and Cellular Pharmacology. 2012; 4:41-48; Yang et al., Nucleic Acids Res. 2006; 34(4):1224-1236; Yang et al., J Biol Chem. 2010; 285(12):8887-8893).

This background information is provided for informational purposes only. No admission is necessarily intended, nor should it be construed, that any of the preceding information constitutes prior art against the present invention.

SUMMARY

It is to be understood that both the foregoing general description of the embodiments and the following detailed description are exemplary, and thus do not restrict the scope of the embodiments.

Described herein is an investigation on whether hnRNP A18 expression levels correlate with tumor grade and an evaluation on whether its regulatory role on protein translation under cellular stress could affect tumor growth and promotion. The data provided herein indicate that hnRNP A18 stabilizes its targeted transcripts and increases de novo protein synthesis under hypoxic conditions. Moreover, hnRNP A18 is over expressed in 40 to 60% of human melanoma, prostate, breast and colon cancer tissue as compared to normal adjacent tissue and down regulation of hnRNP A18 decreases proliferation, invasion and migration in addition to significantly reducing tumor growth in two mouse xenograft models. It is believed that this is the first demonstration that hnRNP A18 can promote tumor growth in in vivo models. hnRNP A18 thus represents a new target to selectively inhibit protein translation in cancer cells and prevent human tumor growth.

According to non-limiting example embodiments, in one aspect, the invention relates to therapeutics which can target hnRNP A18, a regulator of protein translation in cancer cells.

In another aspect, the invention provides a method of treating cancer in a subject, comprising administering to the subject a therapeutically effective amount of a composition that decreases the level and/or activity of heterogenous ribonucleoprotein A18 (hnRNP A18).

In some embodiments, the composition comprises a nucleic acid molecule that comprises a nucleotide sequence that binds to at least a portion of a nucleotide sequence coding for hnRNP A18.

In another aspect, the invention provides a composition for treating cancer comprising a nucleic acid or antibody that is capable of decreasing the level and/or activity of heterogenous ribonucleoprotein A18 (hnRNP A18) and a pharmaceutically acceptable carrier.

In another aspect, the invention provides method for screening for an anti-cancer compound comprising
   i) treating a cancer cell with a candidate compound; and
   ii) detecting whether a level or activity of hnRNP A18 is reduced,
thereby screening the candidate compound for anti-cancer activity.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The skilled artisan will understand that the drawings, described below, are for illustration purposes only. The drawings are not intended to limit the scope of the present teachings in any way.

FIG. 4: hnRNP A18 increases HIF-1α translation. A) Ribonucleoprotein Immunoprecipitation (RNP-IP) on polysomes extracted from cells exposed or not to $CoCl_2$. IP was followed by RT-PCR (26 cycles) to detect endogenous HIF-1α transcript. GAPDH was amplified from the same fractions to confirm that equal amounts of mRNA were present in each immunoprecipitated sample. Densitometry results of three independent experiments were normalized to GAPDH and to the amount of HIF-1α mRNA immunoprecipitated with IgG antibody. B) mRNA stability assay. LOX-IMVI cells stably transfected with either scrambled RNA (solid line or shhnRNP A18 (dashed line) were treated (right panel) or not (left panel) with $CoCl_2$ for 4 hours, then Actinomycin D (10 μg/ml) was added. RNA was collected at the indicated time points, reverse transcribed and analyzed by Real-Time PCR. Data were normalized to GAPDH mRNA and expressed as a percentage of the zero-time point of each respective sample group on nonlinear regression to determine half-life. C) Western blot analysis performed on LOX-IMVI cells (LOX) stably transfected with either scrambled shRNA (sc) or hnRNP A18 shRNA (shA18) were exposed (+) or not (−) to $CoCl_2$ (100 μM, 4 h). Positions of HIF-1α and Actin are indicated. D) Relative levels of HIF-1α measured by densitometry from Western blots. Levels of HIF-1α expression are expressed as a percentage of the LOX-IMVI sc cells exposed to $CoCl_2$. E) Same as C) except that the cells were exposed to 0.5% $O_2$ (hypoxia) or 20% $O_2$ (normoxia) for 24 h. $*p<0.05$, $p<0.005$, $*p<0.0005$

FIG. 12: NCBI Accession numbers and sequence alignment of a hnRNP A18 RNA recognition motif found in the indicated transcripts. Invariant nucleotide [6] are in shaded boxes and the predicted positions of hnRNP A18 motif relative to the 3' UTR start site are indicated in parentheses.

DETAILED DESCRIPTION

Figure 1:
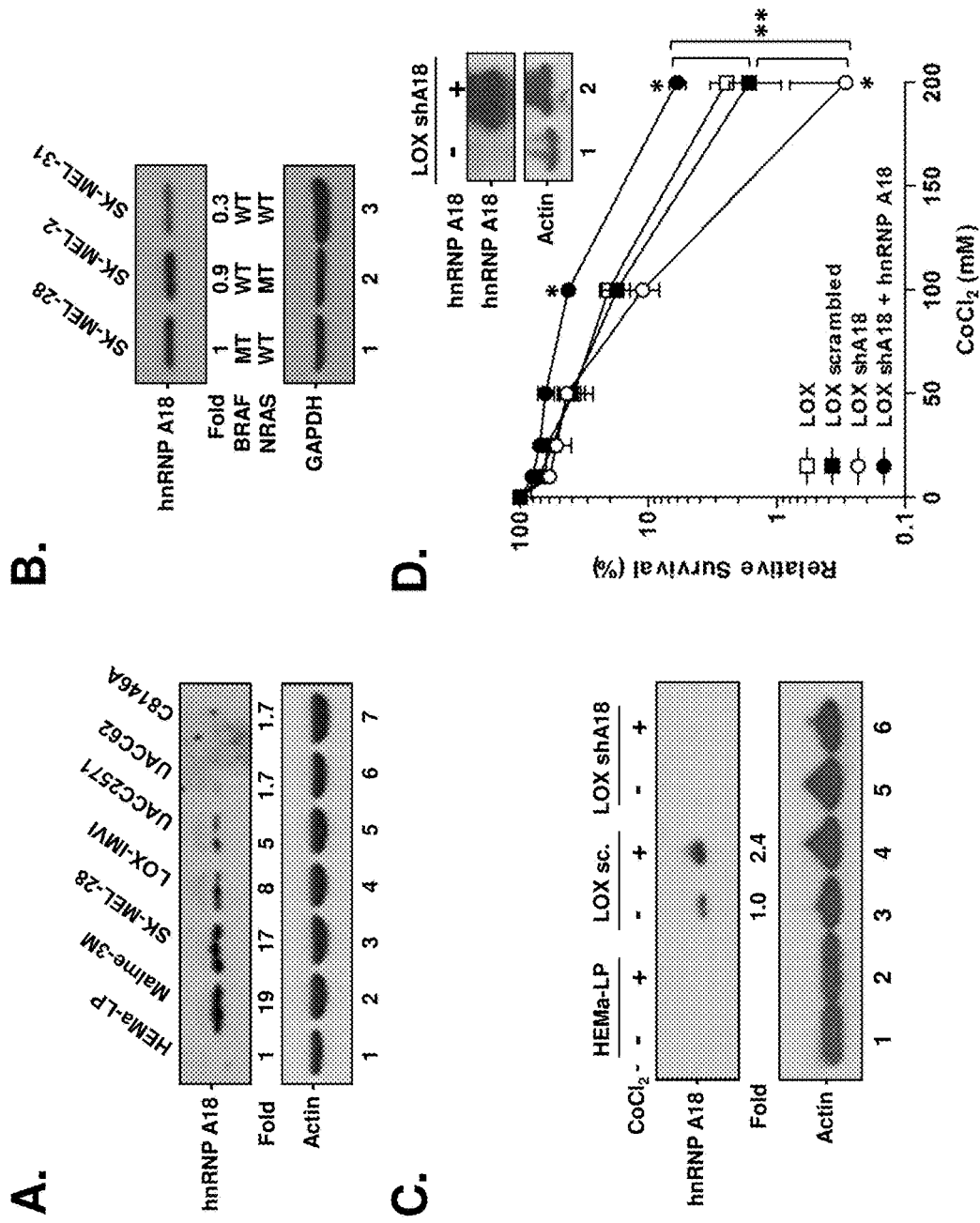
FIG. 1: hnRNP A18 promotes tumor growth under hypoxic conditions. Western blot analysis. A) Normal human melanocytes (HEMa-LP) and six melanoma cell lines were analyzed for hnRNP A18 levels. Fold induction was measured by densitometry and normalized to Actin. B) Melanoma cell lines harboring different BRAF/NRAS genotypes. The blots were hybridized with the indicated antibody. Fold induction was calculated by densitometry and normalized to GAPDH. C) Western Blot. Normal human melanocytes HEMa-LP or LOX-IMVI melanoma cells stably transfected with scrambled (LOX sc) or shhnRNP A18 RNA (LOX shA18) were exposed (+) or not to $CoCl_2$ (100 μM) for 4 h. The blots were hybridized with the indicated antibody. Fold induction was calculated by densitometry and normalized to Actin. D) Relative survival assay performed on LOX-IMVI (open squares), LOX-IMVI stably transfected with scrambled RNA (closed squares), or shhnRNP A18 (open circles) or hnRNP A18 back in LOX-IMVI stably transfected with shhnRNP A18 (closed circles). Cells were exposed to the indicated concentration of $CoCl_2$ and colonies were counted 10 days later. Relative survival is expressed as a percentage of colonies obtained with untreated cells. Inset (D) Western blot analysis. LOX-IMVI cells stably transfected with hnRNP A18 shRNA were re-transfected (+) with hnRNP A18 and analyzed by Western blots with the indicated antibody. $*p<0.05$, $**p<0.005$.

The invention is based on the discovery that the heterogenous ribonucleoprotein A18 (hnRNP A18) promotes tumor growth by coordinating the translation of selected transcripts associated with proliferation and survival. hnRNP A18 binds to and stabilizes the transcripts of pro-survival genes harboring its RNA signature motif in their 3'UTRs. hnRNP A18 binds to ATR, RPA, TRX, HIF-1α and several protein translation factor mRNAs on polysomes and increases de novo protein translation under cellular stress. Most importantly, down regulation of hnRNP A18 decreases proliferation, invasion and migration in addition to significantly reducing tumor growth in two mouse xenograft models, melanoma and breast cancer. Moreover, tissue microarrays performed on human melanoma, prostate, breast and colon cancer indicate that hnRNP A18 is over expressed in 40 to 60% of these malignant tissue as compared to normal adjacent tissue Immunohistochemistry data indicate that hnRNP A18 is over expressed in the stroma and hypoxic areas of human tumors. These data thus indicate that hnRNP A18 can promote tumor growth in in vivo models by coordinating the translation of pro-survival transcripts to support the demands of proliferating cells and increase survival under cellular stress. hnRNP A18 therefore represents a new target to selectively inhibit protein translation in tumor cells.

Unless otherwise noted, technical terms are used according to conventional usage. Definitions of common terms in molecular biology may be found, for example, in Benjamin Lewin, *Genes* VII, published by Oxford University Press, 2000 (ISBN 019879276X); Kendrew et al. (eds.); *The Encyclopedia of Molecular Biology*, published by Blackwell Publishers, 1994 (ISBN 0632021829); and Robert A. Meyers (ed.), *Molecular Biology and Biotechnology: a Comprehensive *Desk Reference*, published by Wiley, John & Sons, Inc., 1995 (ISBN 0471186341); and other similar technical references.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of or means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

In one embodiment, the present invention is directed to a method of treating cancer in a subject, comprising administering to the subject a therapeutically effective amount of a composition that decreases the level and/or activity of heterogenous ribonucleoprotein A18 (hnRNP A18).

The term "subject" as used herein is not limiting and is used interchangeably with patient. In some embodiments, the subject refers to animals, such as mammals. For example, mammals contemplated include humans, primates, dogs, cats, sheep, cattle, goats, pigs, horses, chickens, mice, rats, rabbits, guinea pigs, and the like. The terms "subject" and "patient."

As used herein, "treat" and all its forms and tenses (including, for example, treating, treated, and treatment) can refer to therapeutic or prophylactic treatment. In certain aspects of the invention, those in need thereof of treatment include those already with a pathological condition of the invention (including, for example, a cancer), in which case treating refers to administering to a subject (including, for example, a human or other mammal in need of treatment) a therapeutically effective amount of a composition so that the subject has an improvement in a sign or symptom of a pathological condition of the invention. The improvement may be any observable or measurable improvement. Thus, one of skill in the art realizes that a treatment may improve the patient's condition, but may not be a complete cure of the pathological condition. In other certain aspects of the invention, those in need thereof of treatment include, those in which a pathological condition is to be prevented, in which case treating refers to administering a therapeutically effective amount of a composition to a subject (including, for example, a human or other mammal in need of treatment) at risk of developing a disease or condition such as cancer.

In accordance with the invention, a "therapeutically effective amount" or "effective amount" is administered to the subject. As used herein a "therapeutically effective amount" or "effective amount" is an amount sufficient to decrease, suppress, or ameliorate one or more symptoms associated with the disease or condition.

In some embodiments, the method results in a decrease in growth, proliferation and/or survival of the cancer by decreasing the cancer's tolerance of hypoxic conditions.

"Cancer" refers to leukemias, lymphomas, carcinomas, and other malignant tumors of potentially unlimited growth that can expand locally by invasion and potentially systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor. In some embodiments, the cancer is melanoma, breast cancer, prostate cancer or colon cancer.

In some embodiments, the subject is administered one or more anti-cancer agents and/or radiotherapy in combination with the composition that decreases the level and/or activity of heterogenous ribonucleoprotein A18 (hnRNP A18).

In some embodiments, the anti-cancer agent is selected from the group consisting of Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, CARBOPLATIN-TAXOL, Carfilzomib, Carmubris (Carmustine), Carmustine, Carmustine Implant, Casodex (Bicalutamide), CeeNU (Lomustine) Ceritinib, Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perj eta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), and Zytiga (Abiraterone Acetate).

In some embodiments, the cancer is a cancer with at least a portion thereof existing under hypoxic conditions. Hypoxic conditions are conditions wherein there is an inadequate supply of oxygen.

In some embodiments, the composition useful in the methods of the invention comprises a nucleic acid molecule that comprises a nucleotide sequence that binds to at least a portion of a nucleotide sequence of hnRNP A18. The nucleic acid molecule can be of any length, so long as at least part of the molecule hybridizes sufficiently and specifically to hnRNP A18 mRNA. The nucleic acid molecule can bind to any region of hnRNP A18 mRNA. In some embodiments, the nucleic acid molecule binds to a particular domain of hnRNP A18 mRNA. In some embodiments, the nucleic acid molecule binds to the region of hnRNP A18 mRNA encoding for the arginine, glycine rich domain (RGG). In some embodiments, the nucleotide sequence of hnRNP A18 is shown in SEQ ID NO: 1 (GenBank Accession No. D78134.1). In some embodiments, a region of the nucleic acid molecule is at least 70%, 75%, 80%, 85%, 90%, 91%, 92%, 93%, 94%, 95%, 96%, 97%, 98% or 99% complementary to at least a portion of SEQ ID 1. In some embodiments, the nucleic acid binds to at least a portion of nucleotides at positions 357-437 of SEQ ID NO: 1 (corresponding to the RGG domain). In some embodiments, the nucleic acid binds to the nucleotides at positions 357-437 of SEQ ID NO: 1. In some embodiments, the composition can comprise a DNA molecule, such as an antisense DNA molecule. In some embodiments, the composition can comprise an RNA molecule, such as an anti-sense RNA molecule, a small interfering RNA (siRNA) molecule, or small hairpin RNA (shRNA) molecule, which may or may not be comprised on a vector, including a viral vector (such as an adeno-associated viral vector, an adenoviral vector, a retroviral vector, or a lentiviral vector) or a non-viral vector. In some embodiments, the expression of the DNA or RNA molecule may be regulated by a regulatory region specific to one or more types of cancer.

A target sequence on a target mRNA can be selected from a given cDNA sequence corresponding to the hnRNP A18, in some embodiments, beginning 50 to 100 nt downstream (i.e., in the 3' direction) from the start codon. The target sequence can, however, be located in the 5' or 3' untranslated regions, or in the region nearby the start codon.

In one embodiment, the composition comprises a nucleic acid molecule that comprises a nucleotide sequence that binds to at least a portion of a nucleotide sequence of hnRNP A18 mRNA. In some embodiments, the nucleic acid molecule is a DNA. In some embodiments, the nucleic acid molecule is an RNA.

In some embodiments, the composition comprises an anti-sense DNA. Anti-sense DNA binds with mRNA and prevents translation of the mRNA. The anti-sense DNA can be complementary to a portion of hnRNP A18 mRNA. In some embodiments, the anti-sense DNA is complementary to the entire reading frame of hnRNP A18. In some embodiments, the anti-sense DNA is complementary to the entire reading frame of SEQ ID NO:1. In some embodiments, the antisense DNA is complementary to a portion of SEQ ID NO:1. In some embodiments, the antisense DNA is at least 15 nucleotides, at least 20 nucleotides, at least 25 nucleotides, at least 30 nucleotides, at least 35 nucleotides, at least 40 nucleotides, at least 50 nucleotides, at least 75 nucleotides, at least 100 nucleotides, at least 150 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, at least 1100 nucleotides, at least 1200 nucleotides or at least 1300 nucleotides.

In some embodiments, the composition comprises an anti-sense RNA. Anti-sense RNA binds with mRNA and prevents translation of the mRNA. The anti-sense RNA can be complementary to a portion of hnRNP A18 mRNA. In some embodiments, the anti-sense RNA is complementary to the entire reading frame of hnRNP A18. In some embodiments, the anti-sense RNA is complementary to the entire reading frame of SEQ ID NO:1. In some embodiments, the antisense RNA is complementary to a portion of SEQ ID NO:1. In some embodiments, the antisense RNA is at least 15 nucleotides, at least 20 nucleotides, at least 25 nucleotides, at least 30 nucleotides, at least 35 nucleotides, at least 40 nucleotides, at least 50 nucleotides, at least 75 nucleotides, at least 100 nucleotides, at least 150 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, at least 1100 nucleotides, at least 1200 nucleotides or at least 1300 nucleotides.

In some embodiments, the composition is an siRNA targeting hnRNP A18. SiRNAs are small single or dsRNAs that do not significantly induce the antiviral response common among vertebrate cells but that do induce target mRNA degradation via the RNAi pathway. The term siRNA refers to RNA molecules that have either at least one double stranded region or at least one single stranded region and possess the ability to effect RNA interference (RNAi). It is specifically contemplated that siRNA can refer to RNA molecules that have at least one double stranded region and possess the ability to effect RNAi. The dsRNAs (siRNAs) may be generated by various methods including chemical synthesis, enzymatic synthesis of multiple templates, digestion of long dsRNAs by a nuclease with RNAse III domains, and the like. An "siRNA directed to" at least a particular region of hnRNP A18 means that a particular hnRNP A18 siRNA includes sequences that result in the reduction or elimination of expression of the target gene, i.e., the siRNA is targeted to the region or gene.

The nucleotide sequence of the siRNA is defined by the nucleotide sequence of its target gene. The hnRNP A18 siRNA contains a nucleotide sequence that is essentially identical to at least a portion of the target gene. In some embodiments, the siRNA contains a nucleotide sequence that is completely identical to at least a portion of the hnRNP A18 gene. Of course, when comparing an RNA sequence to a DNA sequence, an "identical" RNA sequence will contain ribonucleotides where the DNA sequence contains deoxyribonucleotides, and further that the RNA sequence will typically contain a uracil at positions where the DNA sequence contains thymidine.

In some embodiments, a hnRNP A18 siRNA comprises a double stranded structure, the sequence of which is "substantially identical" to at least a portion of the target gene. "Identity," as known in the art, is the relationship between two or more polynucleotide (or polypeptide) sequences, as determined by comparing the sequences. In the art, identity also means the degree of sequence relatedness between polynucleotide sequences, as determined by the match of the order of nucleotides between such sequences. Identity can be readily calculated by standard practices in the art.

One of skill in the art will appreciate that two polynucleotides of different lengths may be compared over the entire length of the longer fragment. Alternatively, small regions may be compared. Normally sequences of the same length are compared for a final estimation of their utility in the practice of the present invention. In some embodiments, there is 100% sequence identity between the dsRNA for use as siRNA and at least 15 contiguous nucleotides of the target gene, although a dsRNA having 70%, 75%, 80%, 85%, 90%, or 95% or greater may also be used in the present invention. A siRNA that is essentially identical to a least a portion of the target gene may also be a dsRNA wherein one of the two complementary strands (or, in the case of a self-complementary RNA, one of the two self-complementary portions) is either identical to the sequence of that portion or the target gene or contains one or more insertions, deletions or single point mutations relative to the nucleotide sequence of that portion of the target gene. siRNA technology thus has the property of being able to tolerate sequence variations that might be expected to result from genetic mutation, strain polymorphism, or evolutionary divergence.

In some embodiments, the invention provides an hnRNP A18 siRNA that is capable of triggering RNA interference, a process by which a particular RNA sequence is destroyed (also referred to as gene silencing). In specific embodiments, hnRNP A18 siRNA are dsRNA molecules that are 100 bases or fewer in length (or have 100 base pairs or fewer in its complementarity region). In some embodiments, a dsRNA may be 15, 16, 17, 18, 19, 20, 21, 22, 23, 24, 25, 26, 27, 28, 29, 30, 40, 50, 60, 70, 80, 90, 100 110, 120, 130, 140, 150, 160, 170, 180, 190, 200, 225, 250, 275, 300, 325, 350, 375, 400, 450, 500, 550, 600, 650, 700, 750, 800, 850, 900, 950, or 1000 nucleotides or more in length. In certain embodiments, hnRNP A18 siRNA may be approximately 21 to 25 nucleotides in length. In some cases, it has a two nucleotide 3' overhang and a 5' phosphate. The particular hnRNP A18 RNA sequence is targeted as a result of the complementarity between the dsRNA and the particular hnRNP A18 RNA sequence. It will be understood that dsRNA or siRNA of the disclosure can effect at least a 20, 30, 40, 50, 60, 70, 80, 90 percent or more reduction of expression of a targeted hnRNP A18 RNA in a cancer cell. dsRNA of the invention (the term "dsRNA" will be understood to include "siRNA" and/or "candidate siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule. In some embodiments, the complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 contiguous bases. In some embodiments, long dsRNA are employed in which "long" refers to dsRNA that are 1000 bases or longer (or 1000 base pairs or longer in complementarity region). The term "dsRNA" includes "long dsRNA", "intermediate dsRNA" or "small dsRNA" (lengths of 2 to 100 bases or base pairs in complementarity region) unless otherwise indicated. In some embodiments of the disclosure, dsRNA can exclude the use of siRNA, long dsRNA, and/or "intermediate" dsRNA (lengths of 100 to 1000 bases or base pairs in complementarity region).

It is specifically contemplated that a dsRNA may be a molecule comprising two separate RNA strands in which one strand has at least one region complementary to a region on the other strand. Alternatively, a dsRNA includes a molecule that is single stranded yet has at least one complementarity region as described above (such as when a single strand with a hairpin loop is used as a dsRNA for RNAi). For convenience, lengths of dsRNA may be referred to in terms of bases, which simply refers to the length of a single strand or in terms of base pairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

Strands or regions that are complementary may or may not be 100% complementary ("completely or fully complementary"). It is contemplated that sequences that are "complementary" include sequences that are at least 50% complementary, and may be at least 50%, 60%, 70%, 80%, or 90% complementary. In some embodiments, siRNA generated from sequence based on one organism may be used in a different organism to achieve RNAi of the cognate target gene. In other words, siRNA generated from a dsRNA that corresponds to a human gene may be used in a mouse cell if there is the requisite complementarity, as described above. Ultimately, the requisite threshold level of complementarity to achieve RNAi is dictated by functional capability. It is specifically contemplated that there may be mismatches in the complementary strands or regions. Mismatches may number at most or at least 1, 2, 3, 4, 5, 6, 7, 8, 9, 10, 11, 12, 13, 14, 15, 16, 17, 18, 19, 20, 21, 22, 23, 24, 25 residues or more, depending on the length of the complementarity region.

In some embodiments, the single RNA strand or each of two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or more (including the full-length of a particular's gene's mRNA without the poly-A tail) bases or base pairs. If the dsRNA is composed of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more bases on either or both ends (5' and/or 3') or as forming a hairpin loop between the complementarity regions.

In some embodiments, the strand or strands of dsRNA are 100 bases (or base pairs) or less. In specific embodiments the strand or strands of the dsRNA are less than 70 bases in length. With respect to those embodiments, the dsRNA strand or strands may be from 5-70, 10-65, 20-60, 30-55, 40-50 bases or base pairs in length. A dsRNA that has a complementarity region equal to or less than 30 base pairs (such as a single stranded hairpin RNA in which the stem or complementary portion is less than or equal to 30 base pairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 base pairs or fewer. In some cases, a dsRNA may be processed in the cell into siRNA.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion.

One or both strands of the siRNA of the disclosure can comprise a 3' overhang. As used herein, a "3' overhang" refers to at least one unpaired nucleotide extending from the 3'-end of a duplexed RNA strand.

Thus in some embodiments, the hnRNP A18 siRNA of the invention comprises at least one 3' overhang of from 1 to about 6 nucleotides (which includes ribonucleotides or deoxynucleotides) in length, from 1 to about 5 nucleotides in length, from 1 to about 4 nucleotides in length, or from about 2 to about 4 nucleotides in length.

In some embodiments in which both strands of the hnRNP A18 siRNA molecule comprise a 3' overhang, the length of the overhangs can be the same or different for each strand. In some embodiments, the 3' overhang is present on both strands of the siRNA, and is 2 nucleotides in length. For example, each strand of the hnRNP A18 siRNA of the invention can comprise 3' overhangs of dithymidylic acid ("TT") or diuridylic acid ("uu").

In order to enhance the stability of the present hnRNP A18 siRNA, the 3' overhangs can be also stabilized against degradation. In some embodiments, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2'-deoxythymidine, is tolerated and does not affect the efficiency of RNAi degradation. In particular, the absence of a 2' hydroxyl in the 2'-deoxythymidine significantly enhances the nuclease resistance of the 3' overhang in tissue culture medium.

In some embodiments, the hnRNP A18 siRNA of the invention comprises the sequence AA(N19)TT or NA(N21), where N is any nucleotide. These hnRNP A18 siRNA comprise approximately 30-70% GC, and in some embodiments comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another embodiment, the hnRNP A18 siRNA of the invention comprises the sequence NAR(N17)YNN, where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In some embodiments, the hnRNP A18 siRNA of the disclosure can be targeted to any stretch of approximately 19-25 contiguous nucleotides in any of the target mRNA sequences (the "target sequence"). Techniques for selecting target sequences for siRNA are given, for example, in Tuschl T et al., "The siRNA User Guide," revised Oct. 11, 2002, the entire disclosure of which is herein incorporated by reference. "The siRNA User Guide" is available on the world wide web at a website maintained by Dr. Thomas Tuschl, Department of Cellular Biochemistry, AG 105, Max-Planck-Institute for Biophysical Chemistry, 37077 Gottingen, Germany, and can be found by accessing the website of the Max Planck Institute and searching with the keyword "siRNA." Thus, in some embodiments, the sense strand of the present siRNA comprises a nucleotide sequence identical to any contiguous stretch of about 19 to about 25 nucleotides in the target mRNA.

In some embodiments of the invention, the hnRNP A18 siRNA targets the hnRNP A18 ORF sequence: (5'-GA-GACAGTTACGACAGTTA-3') (SEQ ID NO:2). In some embodiments, the siRNA comprises a 21 nucleotide double stranded sequence comprising SEQ ID NO:11 (5'-GA-GACAGUUACGACAGUUAUU-3') and SEQ ID NO:12 (5'-UAACUGUCGUAACUGUCUCUU-3') corresponding to 19 nucleotides from the hnRNP A18 ORF with a two-TT overhang (Yang et al., Nucleic Acid Research, 34(4), 1224-1236, 2006).

In some embodiments, the composition useful in the methods of the invention comprises an shRNA molecule that targets hnRNP A18 mRNA (hnRNP A18 shRNA). shRNA is an artificial RNA molecule with a tight hairpin turn that can be used to silence target gene expression via RNA interference (RNAi). In certain cases, expression of hnRNP A18 shRNA in cells is achieved through delivery of non-viral vectors (such as plasmids or bacterial vectors) or through viral vectors. shRNA is useful because it has a relatively low rate of degradation and turnover.

In order to obtain long-term gene silencing, expression vectors that continually express siRNAs in stably transfected mammalian cells can be used (Brummelkamp et al., Science 296: 550-553, 2002; Lee et al., Nature Biotechnol. 20:500-505, 2002; Miyagishi, M, and Taira, K. Nature Biotechnol.

20:497-500, 2002; Paddison, et al., Genes & Dev. 16:948-958, 2002; Paul et al., Nature Biotechnol. 20:505-508, 2002; Sui, Proc. Natl. Acad. Sci. USA 99(6):5515-5520, et al., 2002; Yu et al., Proc. Natl. Acad. Sci. USA 99(9):6047-6052, 2002). Many of these plasmids have been engineered to express shRNAs lacking poly (A) tails. Transcription of shRNAs is initiated at a polymerase III (pol III) promoter and is believed to be terminated at position 2 of a 4-5-thymine transcription termination site. Upon expression, shRNAs are thought to fold into a stem-loop structure with 3' UU-overhangs. Subsequently, the ends of these shRNAs are processed, converting the shRNAs into ~21 nt siRNA-like molecules. The siRNA-like molecules can, in turn, bring about gene-specific silencing in the transfected mammalian cells.

The length of the stem and loop of shRNAs can be varied. In some embodiments, stem lengths could range anywhere from 25 to 29 nucleotides and loop size could range between 4 to 23 nucleotides without affecting silencing activity. Moreover, presence of G-U mismatches between the two strands of the shRNA stem does not necessarily lead to a decrease in potency.

In some embodiments, the present invention is directed towards methods of administering subjects with compositions comprising expression vectors and/or chemically synthesized shRNA molecules that target hnRNP A18. In some embodiments, the composition comprises a nucleotide sequence expressing a small hairpin RNA (shRNA) molecule. In some embodiments, the shRNA molecule is expressed by an expression vector comprising one or more of SEQ ID NOS: 3, 4, 5 or 6. In some embodiments, the expression vector is a lentivirus expression vector.

In some embodiments, it is contemplated that nucleic acids or antibodies of the invention may be labeled. The label may be fluorescent, radioactive, enzymatic, or calorimetric. It is contemplated that a dsRNA may have one label attached to it or it may have more than one label attached to it. When more than one label is attached to a dsRNA, the labels may be the same or be different. If the labels are different, they may appear as different colors when visualized. The label may be on at least one end and/or it may be internal. Furthermore, there may be a label on each end of a single stranded molecule or on each end of a dsRNA made of two separate strands. The end may be the 3' and/or the 5' end of the nucleic acid. A label may be on the sense strand or the sense end of a single strand (end that is closer to sense region as opposed to antisense region), or it may be on the antisense strand or antisense end of a single strand (end that is closer to antisense region as opposed to sense region). In some cases, a strand is labeled on a particular nucleotide (G, A, U, or C). When two or more differentially colored labels are employed, fluorescent resonance energy transfer (FRET) techniques may be employed to characterize the dsRNA.

Labels contemplated for use in several embodiments are non-radioactive. In many embodiments of the invention, the labels are fluorescent, though they may be enzymatic, radioactive, or positron emitters. Fluorescent labels that may be used include, but are not limited to, BODIPY, Alexa Fluor, fluorescein, Oregon Green, tetramethylrhodamine, Texas Red, rhodamine, cyanine dye, or derivatives thereof. The labels may also more specifically be Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, DAPI, 6-FAM, Killer Red, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, TET, Tetramethylrhodamine, and/or Texas Red. A labeling reagent is a composition that comprises a label and that can be incubated with the nucleic acid to effect labeling of the nucleic acid under appropriate conditions. In some embodiments, the labeling reagent comprises an alkylating agent and a dye, such as a fluorescent dye. In some embodiments, a labeling reagent comprises an alkylating agent and a fluorescent dye such as Cy3, Cy5, or fluorescein (FAM). In still further embodiments, the labeling reagent is also incubated with a labeling buffer, which may be any buffer compatible with physiological function (i.e., buffers that is not toxic or harmful to a cell or cell component) (termed "physiological buffer").

In some embodiments, the nucleic acids of the invention can be modified. In some embodiments, the nucleic acids can be modified to include a phosphorothioate (PS) backbone. The modification to the backbone can be throughout the molecule or at one or more defined sites. In some embodiments, the nucleic acids can be modified to encompass peptide nucleic acids (PNA). In some embodiments, the nucleic acids can be modified to encompass phosphorodiamidate morpholino oligomers (PMO).

In some embodiments, the nucleic acid molecules of the invention can include derivatives such as S-oligonucleotides (phosphorothioate derivatives or S-oligos). S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer et al., J. Org. Chem. 55:4693-4698 (1990); and Iyer et al., J. Am. Chem. Soc. 112:1253-1254 (1990), the disclosures of which are fully incorporated by reference herein.

In some embodiments of the invention, a dsRNA has one or more non-natural nucleotides, such as a modified residue or a derivative or analog of a natural nucleotide. Any modified residue, derivative or analog may be used to the extent that it does not eliminate or substantially reduce (by at least 50%) RNAi activity of the dsRNA.

A person of ordinary skill in the art is well aware of achieving hybridization of complementary regions or molecules. Such methods typically involve heat and slow cooling of temperature during incubation, for example.

In some embodiments, the nucleic acid molecules of the present methods are encoded by expression vectors. The expression vectors may be obtained and introduced into a cell. Once introduced into the cell the expression vector is transcribed to produce various nucleic acids. Expression vectors include nucleic acids that provide for the transcription of a particular nucleic acid. Expression vectors include plasmid DNA, linear expression elements, circular expression elements, viral expression constructs (including adenoviral, adeno-associated viral, retroviral, lentiviral, and so forth), and the like, all of which are contemplated as being used in the compositions and methods of the present disclosure. In some embodiments one or at least 2, 3, 4, 5, 6, 7, 8, 9, 10 or more nucleic acid molecules binding to hnRNP A18 RNA are encoded by a single expression construct. Expression of the nucleic acid molecules binding to hnRNP A18 RNA may be independently controlled by at least 2, 3, 4, 5, 6, 7, 8, 9, 10 or more regulatory elements. In certain embodiments, at least 2, 3, 4, 5, 6, 7, 8, 9, 10 or more expression constructs can be introduced into a cell. Each expression construct can encode 1, 2, 3, 4, 5, 6, 7, 8, 9, 10 or more nucleic acid molecules binding to hnRNP A18

RNA. In some embodiments, nucleic acid molecules binding to hnRNP A18 RNA may be encoded as expression domains. Expression domains include a transcription control element, which may or may not be independent of other control or promoter elements; a nucleic acid; and optionally a transcriptional termination element.

Any suitable viral vector can be used in the methods of the invention. For example, vectors derived from adenovirus (AV); adeno-associated virus (AAV; including AAV serotypes); retroviruses (e.g, lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector of the invention can be pseudotyped with surface proteins from vesicular stomatitis virus (VSV), rabies, Ebola, Mokola, and the like.

Selection of recombinant viral vectors suitable for use in the invention, are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; and Anderson W F (1998), Nature 392: 25-30, the entire disclosures of which are herein incorporated by reference.

The ability of a RNA of the claimed invention to cause RNAi-mediated degradation of the target mRNA can be evaluated using standard techniques for measuring the levels of RNA or protein in cells. For example, hnRNP A18 siRNA of the invention can be delivered to cultured cells, and the levels of target mRNA can be measured by Northern blot or dot blotting techniques, or by quantitative RT-PCR. Alternatively, the levels of hnRNP A18 protein in the cultured cells can be measured by ELISA or Western blot. A suitable cell culture system for measuring the effect of the present siRNA on target mRNA or protein levels may be utilized. RNAi-mediated degradation of hnRNP A18 mRNA by an siRNA containing a given target sequence can also be evaluated with animal models, for example.

In other embodiments, the method comprises administering a composition comprising an antibody that reduce activity of hnRNP A18. As used herein, the term "antibody" includes any immunologic binding agent, such as IgG, IgM, IgA, IgD and IgE. Generally, IgG and/or IgM may be utilized because they are the most common antibodies in the physiological situation and because they are most easily made in a laboratory setting. The term "antibody" may be used to refer to any antibody-like molecule that has an antigen binding region, and includes antibody fragments such as Fab', Fab, F(ab')2, single domain antibodies (DABs), Fv, scFv (single chain Fv), and the like. Monoclonal and humanized antibodies are also contemplated in the disclosure.

In some embodiments, the nucleic acids can be administered to the subject either as naked nucleic acid, in conjunction with a delivery reagent, or as a recombinant plasmid or viral vector that expresses the nucleic acids. Delivery of nucleic acids or vectors to an individual may occur by any suitable means, but in specific embodiments it occurs by one of the following: cyclodextrin delivery system; ionizable lipids; DPC conjugates; GalNAc-conjugates; self-assembly of oligonucleotide nanoparticles (DNA tetrahedra carrying multiple siRNAs); or polymeric nanoparticles made of low-molecular-weight polyamines and lipids (see Kanasty et al. Nature Materials 12, 967-977 (2013) for review of same).

Suitable delivery reagents for administration in conjunction with the present nucleic acids or vectors include at least the Mirus Transit TKO lipophilic reagent; lipofectin; lipofectamine; cellfectin; or polycations (e.g., polylysine), or liposomes. In specific embodiments, a particular delivery reagent comprises a liposome.

Liposomes can aid in the delivery of the present nucleic acids or vectors to a particular tissue, and can also increase the blood half-life of the nucleic acids. Liposomes suitable for use in the invention are formed from standard vesicle-forming lipids, which generally include neutral or negatively charged phospholipids and a sterol, such as cholesterol. The selection of lipids is generally guided by consideration of factors such as the desired liposome size and half-life of the liposomes in the blood stream. A variety of methods are known for preparing liposomes, for example as described in Szoka et al. (1980), Ann. Rev. Biophys. Bioeng. 9: 467; and U.S. Pat. Nos. 4,235,871, 4,501,728, 4,837,028, and 5,019,369, the entire disclosures of which are herein incorporated by reference.

In certain aspects, the liposomes encapsulating the present nucleic acids comprise a ligand molecule that can target the liposome to a particular cell or tissue at or near the site of interest. Ligands that bind to receptors prevalent in the tissues to be targeted, such as monoclonal antibodies that bind to surface antigens, are contemplated. In particular cases, the liposomes are modified so as to avoid clearance by the mononuclear macrophage and reticuloendothelial systems, for example by having opsonization-inhibition moieties bound to the surface of the structure. In one embodiment, a liposome of the invention can comprise both opsonization-inhibition moieties and a ligand. Opsonization-inhibiting moieties for use in preparing the liposomes of the disclosure are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer which significantly decreases the uptake of the liposomes by the macrophage-monocyte system ("MMS") and reticuloendothelial system ("RES"); e.g., as described in U.S. Pat. No. 4,920,016, the entire disclosure of which is herein incorporated by reference. Liposomes modified with opsonization-inhibition moieties thus remain in the circulation much longer than unmodified liposomes. For this reason, such liposomes are sometimes called "stealth" liposomes.

Stealth liposomes are known to accumulate in tissues fed by porous or "leaky" microvasculature. Thus, target tissue characterized by such microvasculature defects, for example solid tumors, will efficiently accumulate these liposomes; see Gabizon, et al. (1988), P.N.A.S., USA, 18: 6949-53. In addition, the reduced uptake by the RES lowers the toxicity of stealth liposomes by preventing significant accumulation in the liver and spleen. Thus, liposomes of the invention that are modified with opsonization-inhibition moieties can deliver the present nucleic acids to tumor cells.

Opsonization inhibiting moieties suitable for modifying liposomes are preferably water-soluble polymers with a number-average molecular weight from about 500 to about 40,000 Daltons, and more preferably from about 2,000 to about 20,000 Daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GME Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups.

In some embodiments the opsonization-inhibiting moiety is a PEG, PPG, or derivatives thereof. Liposomes modified with PEG or PEG-derivatives are sometimes called "PEGylated liposomes." The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH 3 and a solvent mixture such as tetrahydrofuran and water in a 30:12 ratio at 60 degrees C.

Recombinant plasmids that express nucleic acids of the invention are discussed above. Such recombinant plasmids can also be administered directly or in conjunction with a suitable delivery reagent, including the Mirus Transit LT 1 lipophilic reagent; lipofectin; lipofectamine; cellfectin; polycations (e.g., polylysine) or liposomes.

The nucleic acids reducing the level of hnRNP A18 of the invention can be administered to the subject by any suitable means. For example, the nucleic acids can be administered by gene gun, electroporation, or by other suitable parenteral or enteral administration routes, or by injection, for example, by intramuscular or intravenous injection. In embodiments wherein composition(s) are delivered to the brain, one either inject into the ventricles or local injection into particular brain regions, for example.

Suitable parenteral administration routes include intravascular administration (e.g. intravenous bolus injection, intravenous infusion, intra-arterial bolus injection, intra-arterial infusion and catheter instillation into the vasculature); peri- and intra-tissue administration (e.g., peri-tumoral and intra-tumoral injection, intra-retinal injection or subretinal injection); subcutaneous injection or deposition including subcutaneous infusion (such as by osmotic pumps); direct (e.g., topical) application to the area at or near the site of interest, for example by a catheter or other placement device (e.g., a corneal pellet or a suppository, eye-dropper, or an implant comprising a porous, non-porous, or gelatinous material); and inhalation. In a particular embodiment, injections or infusions of the composition(s) are given at or near the site of disease.

The nucleic acids reducing the level of hnRNP A18 of the invention can be administered in a single dose or in multiple doses. Where the administration of a composition is by infusion, the infusion can be a single sustained dose or can be delivered by multiple infusions. Injection of the agent directly into the tissue is at or near the site of need. Multiple injections of the agent into the tissue at or near the site of interest are encompassed within this disclosure.

One skilled in the art can also readily determine an appropriate dosage regimen for administering the nucleic acids reducing the level of hnRNP A18 of the invention to a given subject. For example, the composition(s) can be administered to the subject once, such as by a single injection or deposition at or near the site of interest. In some embodiments, the composition(s) can be administered to a subject once or twice daily to a subject once weekly for a period of from about three to about twenty-eight days, in some embodiments, from about seven to about ten weeks. In some dosage regimens, the composition(s) is injected at or near the site of interest once a day for seven days. Where a dosage regimen comprises multiple administrations, it is understood that the effective amount of composition(s) administered to the subject can comprise the total amount of composition(s) administered over the entire dosage regimen.

In one embodiment, the present invention is directed towards a composition for treating cancer comprising an isolated nucleic acid that decreases the level and/or activity of heterogenous ribonucleoprotein A18 (hnRNP A18) and a pharmaceutically acceptable carrier. In some embodiments, the nucleic acid comprises SEQ ID NO:1 or a fragment thereof capable of decreasing the level and/or activity of heterogenous ribonucleoprotein A18 (hnRNP A18). In some embodiments, the nucleic acid comprises SEQ ID NOS:2, 3, 4, 5, 6, or xx.

The composition(s) of the disclosure may be formulated as pharmaceutical compositions prior to administration to a subject, according to techniques known in the art. See, e.g., Remington's Pharmaceutical Science, 17th ed., Mack Publishing Company, Easton, Pa. (1985), the entire disclosure of which is herein incorporated by reference. In some embodiments, pharmaceutical compositions of the present invention are characterized as being at least sterile and pyrogen-free. As used herein, "pharmaceutical formulations" include formulations for human and veterinary use.

Pharmaceutical compositions of the disclosure can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid compositions, conventional nontoxic solid carriers can be used; for example, pharmaceutical grades of mannitol, lactose, starch, magnesium stearate, sodium saccharin, talcum, cellulose, glucose, sucrose, magnesium carbonate, and the like. For example, a solid pharmaceutical composition for oral administration can comprise any of the carriers and excipients listed above and 10-95%, or 25%-75%, of one or more compositions of the invention. In some embodiments, a pharmaceutical composition for aerosol (inhalational) administration can comprise 0.01-20% by weight or 1%40% by weight, of one or more compositions of the invention encapsulated in a liposome as described above, and propellant. A carrier can also be included as desired; e.g., lecithin for intranasal delivery.

Methods of Screening for Anti-cancer Agent

In one embodiment, the present invention is directed towards methods of screening for anti-cancer compounds comprising treating a cancer cell with a candidate anti-cancer agent, and detecting whether a level or activity of hnRNP A18 is reduced, thereby screening the candidate compound for anti-cancer activity.

In some embodiments, the ability of inhibitors to interfere with hnRNP A18 can be evaluated. In some embodiments, the assay can be conducted in vitro to determine whether the inhibitors reduce the interaction between the hnRNP A18 and its binding partners. In some embodiments of the invention, an assay for hnRNP A18 activity in cells can be used to determine the functionality of the hnRNP A18 in the presence of an agent which may act as an inhibitor, and thus, agents that interfere with the activity of hnRNP A18 can be identified.

In some embodiments, the hnRNP A18 of the present invention is employed in a screening process for compounds which bind hnRNP A18 or one of its binding partners or both and which inhibits the biological activity of the hnRNP A18 interaction Inhibitors of hnRNP A18 are particularly advantageous and can be used in methods as therapeutic agents in the treatment of cancer, such as melanoma, breast cancer, prostate cancer or colon cancer.

By "inhibitor" is intended naturally occurring and/or synthetic agents capable of inhibiting hnRNP A18 interactions with its target transcripts.

In some embodiments, the screening procedures involve producing appropriate cells which produce hnRNP A18. Such cells can include cells from mammals, yeast, *Drosophila* or *E. coli*. In some embodiments, the cells express hnRNP A18 endogenously. In other embodiments, the cells have been transfected or engineered to express hnRNP A18. In some embodiments, cells expressing hnRNP A18 (or extracts or purified preparations from cells) are contacted with a test compound to observe stimulation or inhibition of a functional response.

In some embodiments, assays can test binding of hnRNP A18 to its target transcripts or assays can involve competition with a competitor compound, such as a labeled competitor.

Potential antagonists are not limiting and examples include antibodies, peptides, carbohydrates, or small molecules which bind to hnRNP A18 or to its target transcripts. These agents can be selected and screened 1) at random, 2) by a rational selection or 3) by design using for example, ligand modeling techniques (e.g., computer modeling).

For random screening, agents such as antibodies, peptides, carbohydrates, pharmaceutical agents and the like are selected at random and are assayed for their ability to bind to or block the interaction of the hnRNP A18 to its target transcripts.

Alternatively, agents may be rationally selected or designed. As used herein, an agent is said to be "rationally selected or designed" when the agent is chosen based on the configuration of the hnRNP A18 or its target transcripts.

In one aspect, the invention provides a method of screening for an anti-cancer agent which inhibits hnRNP A18, comprising: (a) contacting hnRNP A18 or a target transcript; and (b) assaying the agent's effect on the hnRNP A18 activity. In some embodiments, the activity to be tested is hnRNP A18 and target transcript binding, and/or biological activity that results from hnRNP A18 and target transcript interaction. In some embodiments, the activity is the production of angiogenic factors in response to hypoxic conditions or mimetics of hypoxic conditions (e.g., $CoCl_2$). In some embodiments, the activity is the productions or levels of angiogenic factors, for example, angiogenin, endoglin and/or VEGF.

In another aspect, the invention provides a method for identifying inhibitors that prevent binding of hnRNP A18 and its target transcript, comprising contacting the hnRNP A18 and its target transcript with the inhibitor and detecting whether the inhibitor prevents binding of the hnRNP A18 and its target transcript. In the cytosol, hnRNP A18 binds to a specific 51 nucleotide RNA signature motif present in the 3' UTR of targeted transcripts and increases their translation by interacting with eukaryotic initiation factor 4G (eIF4G), a component of the general translation cap-binding complex eIF4F, on polysomes. In some embodiments, the screening method comprises contacting the hnRNP A18 and the specific 51 nucleotide RNA signature motif with the inhibitor and detecting whether the inhibitor prevents binding of the hnRNP A18 and the specific 51 nucleotide RNA signature motif. In some embodiments, the screening method comprises contacting the hnRNP A18 complexed with the specific 51 nucleotide RNA signature motif and eIF4G with the inhibitor and detecting whether the inhibitor prevents binding of the hnRNP A18/specific 51 nucleotide RNA signature motif complex and eIF4G.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto).

EXAMPLES

Example 1

Heterogenous ribonucleoprotein A18 (hnRNP A18) promotes tumor growth by increasing protein translation of selected transcripts in cancer cells.

In this example, it is shown that the heterogenous ribonucleoprotein A18 (hnRNP A18) promotes tumor growth by coordinating the translation of selected transcripts associated with proliferation and survival. hnRNP A18 binds to and stabilizes the transcripts of pro-survival genes harboring its RNA signature motif in their 3'UTRs. hnRNP A18 binds to ATR, RPA, TRX, HIF-1α and several protein translation factor mRNAs on polysomes and increases de novo protein translation under cellular stress. Most importantly, down regulation of hnRNP A18 decreases proliferation, invasion and migration in addition to significantly reducing tumor growth in two mouse xenograft models, melanoma and breast cancer. Moreover, tissue microarrays performed on human melanoma, prostate, breast and colon cancer indicate that hnRNP A18 is over expressed in 40 to 60% of these malignant tissue as compared to normal adjacent tissue Immunohistochemistry data indicate that hnRNP A18 is over expressed in the stroma and hypoxic areas of human tumors. These data thus indicate that hnRNP A18 can promote tumor growth in in vivo models by coordinating the translation of pro-survival transcripts to support the demands of proliferating cells and increase survival under cellular stress. hnRNP A18 therefore represents a new target to selectively inhibit protein translation in tumor cells.

Material and Methods

Cell lines and treatments—Human malignant melanoma cell lines were obtained and grown as described previously (Yang et al., J Biol Chem. 2010; 285(12):8887-8893). The normal Human Epidermal Melanocytes, adult, HEMa-LP were purchased from Life Technology (Invitrogen) and maintained in Medium 254 supplemented with Human Melanocyte Growth Supplement-2 (HMGS-2). The human breast cancer cell line MDA-MB-231 was purchased from ATCC (Manassas, Va.) and grown in DMEM (Dulbeco's Modified Eagle Medium) with high glucose supplemented with 10% Fetal Bovine Serum.

Cells proliferation, invasion and migration—Real-time monitoring of proliferation, invasion, and migration were performed on the xCELLigence RTCA MP Instrument from ACEA Biosciences, Inc. (ACEA) according to manufacturer's instructions. For the proliferation assay, MDA-MB-231 scrambled and MDA-MB-231 shLentiA18 cells (5,000 cells/well) were plated in triplicates in 96× microplates (E-Plate) and monitored every 15 minutes for a total of 120 hours. In the invasion and migration experiments, MDA-MB-231 scrambled and MDA-MB-231 shLentiA18 cells (75,000 cells/well) were seeded without FBS into the upper chamber of a CIM-Plate 16. Complete growth medium supplemented with 10% FBS (or no FBS as negative control) was added in the lower chamber as a chemoattractant. CIM-Plate 16 was loaded into the xCELLigence RTCA MP Instrument for real-time monitoring at 15-minute intervals for 48 hours. Conventional migration assays were carried out in Transwell Boyden chambers (Corning costar) with polycarbonate filters (8 µm pores). LOX-IMVI ($2.5\times10^4$) cells stably expressing scrambled or shhnRNP A18, were added to the upper chamber without serum while the lower chamber contained growth media with 10% FBS. After incubation for 24 h at 37° C., non-migrating cells were removed by sterile cotton swab. Cells that migrated to the lower surface were fixed in 100% methanol and stained with 0.1% (w/v) crystal violet solution. Images of cells from three different areas were taken and counted. Experiments were done twice in triplicates and data was presented as the average number of cells which migrated. MATRIGEL invasion assay was carried out essentially as described above (migration assay) except that Corning MATRIGEL Invasion chambers with polycarbonate filters (8 µm pores) were used.

Cells transfection with shRNA-LOX-IMVI cells were stably transfected (FuGene HD, Promega) with four different shRNA vectors for hnRNP A18 or a mixture of the four vectors (1 µg total, OriGene, Rockville, Md.) or scrambled RNA and selected with Puromycin (0.5 µg/ml) for 2 weeks. Where indicated, stable LOX-IMVI cells transfected with shhnRNP A18 were re-transfected with hnRNP A18-GFP (Yang C and Carrier F., J Biol Chem. 2001; 276(50):47277-47284) and selected with Hygromycin (50 µg/ml) for two weeks. Parent LOX-IMVI cells were also stably transfected with hnRNP A18-GFP and selected with Hygromycin for two weeks. For animal studies, LOX-IMVI and MDA-MB-231 cells were stably transfected with scrambled or shhnRNP A18 lentivirus with Mission lentiviral packaging mix (Cat #SHP 001, Sigma Aldrich, St. Louis, Mo.) according to the manufacturer's instructions. Briefly HEK-293T cells were transfected with pGFP-C-shhnRNP A18 lenti (TL313897 A-D) or pGFP-CSh scrambled lenti (TR-30021) (OriGene, Rockville, Md.) and packaging plasmids using FuGene 6 (Promega). Detection of GFP expression and Western blotting for hnRNP A18 were carried out to determine infection efficiency.

Animal studies—LOX-IMVI and MDA-MB-231 cells stably transfected with either a vector expressing a scrambled shRNA sequence or a mixture of four plasmids expressing different hnRNP A18 shRNAs (LOX-IMVI) or shhnRNP A18-B (MDA-MB-231) were injected s.c. in the flanks of six to eight four-week-old female athymic mice (nu/nu). The mice received $3\times10^6$ cells transfected with shhnRNP A18 in 100 µl plus MATRIGEL in the left flank or $3\times10^6$ LOX-IMVI stably transfected with scrambled shRNA on the right flank. Tumors were allowed to grow for 15 to 35 days, volumes measured by caliper at different intervals, then the mice were sacrificed and the tumors were excised and weighed.

Clonogenic Survival assays—Clonogenic survival assays were performed as described previously (Yang C and Carrier F., J Biol Chem. 2001; 276(50):47277-47284). Briefly, $3\times10^2$ cells were plated in 6-well plates and exposed to increasing concentrations of $CoCl_2$ for 48 h. The cells were then replenished with fresh media and colonies were counted 7-10 days later. Treatments were performed in triplicate for each dose.

Tissue Microarrays—Immunohistochemistry was performed on sections of 295 primary human tumors with built-in adjacent tissues. The slides were prepared with an immunohistochemistry kit (Pantomics Mini IHC Kit) according to the manufacturer recommendations. Briefly, the slides were baked in an oven at 60° C. for 60 min and deparaffinized with xylene for 5 min, twice. The sections were then rehydrated through a series of washes with decreasing ethanol concentration (100-70%) and soaked in water. Endogenous peroxide activity was inactivated and heat-induced antigen retrieval was performed. The slides were then heated for 5 min in a conventional pressure cooker at moderate power. After incubating the slides in pre-blocking solution, the slides were incubated with hnRNP A18/CIRP rabbit polyclonal antibody (Abcam) at 1/1000 and 1/2000 dilutions for 1 h. Secondary antibody conjugated to horseradish peroxidase was then used and the slides were reacted with DAB substrate. The sections were counterstained with Mayer's Hematoxylin and mounted on coverslips. Rabbit antibody to cytokeratin and normal rabbit serum were used as positive and negative controls. Immunohistological staining of tissue microarrays for hnRNP A18 was scored blindly by a pathologist at Pantomics, Inc. (Richmond, Calif.) using the following criteria: "0"=negative; "0.5"=negative with some weak but suspicious staining; "1"=weak staining; "2"=moderate staining; "3"=strong staining. Scores for hnRNP A18 were then tabulated and expressed as a percentage of the respective cases analyzed.

Ribonucleoprotein (RNP) immunoprecipitation—RNA bound to hnRNP A18 was immunoprecipitated as described (Tenenbaum et al., Methods. 2002; 26(2):191-198; Yang et al., Nucleic Acids Res. 2006; 34(4):1224-1236; Yang et al., J Biol Chem. 2010; 285(12):8887-8893). Briefly the cells were lysed with polysome lysis buffer (10 mM Hepes, pH 7.0, 100 mM KCl, 5 mM $MgCl_2$, 0.5% NP-40) and total lysates (1.5 mg) were incubated in the presence of EDTA (20 mM) with protein A-Sepharose CL-4B beads (Sigma) that had been pre-coated with 30 µg of either anti-hnRNP A18/CIRP (Sigma, cat: 121-135) or Normal rabbit anti-IgG1 (Calbiochem, Cat: NI01)). The beads were washed six times with NT2 buffer (50 mM Tris-HCl (pH 7.5), 150 mM NaCl, 1 mM $MgCl_2$ and 0.05% NP-40) and then incubated with 100 µl NT2 buffer containing 20 U RNase free DNase I for 15 min at 37° C. Bound proteins were then digested by adding 0.1% SDS and 0.5 mg/ml proteinase K and the reactions were continued for 15 min at 55° C. RNA was extracted by ethanol precipitation and used to perform RT-PCR. The PCR products were visualized after electrophoresis in 1% agarose gels.

```
Primers for RT-PCR were:
HIF-1α:
5'>AACCCATTCCTCACCCATCA<3',        (SEQ ID NO: 7)

5'>TCCACCTCTTTTGGCAAGCA<3',        (SEQ ID NO: 8)
```

-continued

GAPDH:
5'>ACATCAAGAAGGTGGTGAAGCAGG<3',     (SEQ ID NO: 9)

5'>CCAGCAAGGATACTGAGAGCAAGAG<3'.    (SEQ ID NO: 10)

Where indicated the cells were exposed to $CoCl_2$ (200 µM) for 2.5 hr prior to immunoprecipitation.

mRNA stability assay—Cells were pre-treated with $CoCl_2$ for 4 hours, then Actinomycin D (10 µg/ml) was added to inhibit transcription. RNA was collected at predetermined time points of 0 h, 2 h, 4 h, 6 h, and 8 h by RNeasy Mini Kit (Qiagen), then reverse transcribed with the Reverse Transcription System (Promega). Resulting complementary DNA (cDNA) was combined with Real-Time TaqMan Gene Expression Assays primers for HIF-1α and GAPDH and then run on the Applied Biosystems 7300 Real-Time PCR System. Data was normalized relative to GAPDH and non-linear regression analysis was used to determine half-life.

Western blots—Human tissues were obtained from the University of Maryland Medical Center, Pathology Biorepository, Research Core. Rabbit polyclonal hnRNP A18 antibody was produced and purified in our laboratory and also purchased from Sigma (CIRP) and used at 1/500 dilution.

HIF-1α, mouse was from Cell Signaling Technologies and used at 1/1000 dilution. Actin mouse monoclonal antibody was from Abcam and used at 1/2000 dilutions. Secondary antibody and protein detection procedure were as described before (Yang et al., Nucleic Acids Res. 2006; 34(4):1224-1236).

De novo protein synthesis—The Click-iT® Metabolic Labeling Reagents for Proteins (Invitrogen) kit was performed in the presence or absence of $CoCl_2$, according to manufacturer's instructions. Briefly, cells were cultured in RPMI methionine-free media for 1 hour, then incubated in the same media with Click-iT® HPG (L-homopropargyl-glycine) for 4 hours. Proteins were extracted and the Click-iT® Protein Reaction Buffer Kit (Invitrogen) was used to label alkyne-tagged proteins with azide-biotin via a $CuSO_4$ catalytic reaction. TRX antibody was incubated with the newly biotinylated protein lysate overnight, then protein A beads were added for 2 hours. Beads were washed 3 times and proteins were run on a SDS-PAGE gel. Newly synthesized proteins were detected by chemiluminescent with anti-Streptavidin-HRP antibody. Actin was used as loading control.

Angiogenesis Proteome Profiler Array—Human Angiogenesis Proteome Profiler Array was performed as described by the manufacturer (R&D Systems Inc., Minneapolis, Minn.). Briefly, 300 µg of proteins extracted from Lox scrambled and Lox shLentiA18 mice xenograft tumors were incubated with Array Buffer 4, Array Buffer 5, and Detection Antibody Cocktail at room temperature for 1 hour. Simultaneously, nitrocellulose membranes spotted in duplicate with capture antibodies to 55 specific angiogenesis-related human proteins were blocked in Array Buffer 7. After 1 hour, Array Buffer 7 was removed and sample/antibody mixtures were added to the membranes for overnight incubation. Membranes were washed with 1× Wash Buffer the following morning, incubated with Streptavidin-HRP, then detected with Chemi Reagent Mix on autoradiographic film. Positive signals were analyzed by densitometry and expressed as mean pixels density after subtracting background. Transfection with siRNA: Lox-IMVI cells were transiently transfected with siRNA directed against HIF-1α (Thermo Fisher Scientific, Waltham, Mass.) using siPORT™ NeoFX Transfection Agent (Thermo Fisher Scientific, Waltham, Mass.) according to manufacturer's instructions. Briefly, HIF-1αsiRNA and siPORT NeoFX were diluted separately in Opti-MEM and incubated for 10 min Following incubation, the diluted transfection agent and siRNA were combined and allowed to incubate for another 10 min in order to allow transfection complexes to form. The mixture was then dispensed into 60 mm plates (for Western blot analysis) or 96-well plates (for WST-1 proliferation assay) and Lox-IMVI cells were overlaid onto transfection complexes. Cell Proliferation Assay: Cell viability and proliferation were assessed using the Cell Proliferation Reagent WST-1 (Roche Diagnostics Corporation, Indianapolis, Ind.). Following transient transfection with HIF-1α siRNA, cells were incubated for 48 hours to allow for the down-regulation of HIF-1α. Cobalt chloride ($CoCl_2$) was then added and cells were allowed to incubate in a hypoxia chamber (0.5% $O_2$) for an additional 24 hours. Following $CoCl_2$ treatment, WST-1 reagent was then added to cells and absorbance was obtained by a multi-well ELISA plate reader.

Statistical analysis—Statistical analysis was performed on the relative (%) ratios of survival colonies expressing reduced levels of hnRNP A18 (shhnRNP A18) over wild type cells, on the weight of tumors stably transfected with shhnRNP A18 over tumor developing with the parent cell line and on HIF-1α relative levels of expression. All calculations including calculations for proliferation, invasion and migration, were performed by the Student t test. Probability values <0.05 are considered significant.

Results hnRNP A18 up-regulation confers growth advantages to melanoma cells under hypoxic conditions.

Given that hnRNP A18 was originally cloned on the basis of UV induction (Fornace et al., Proc Natl Acad Sci USA. 1988; 85(23):8800-8804) and that it can confer resistance to UV-induced cellular death (Yang C and Carrier F., J Biol Chem. 2001; 276(50):47277-47284), the goal was to investigate whether hnRNP A18 could also be involved in the UV-induced skin cancer melanoma.

The levels of hnRNP A18 protein were thus analyzed in six different melanoma cell lines and compared to normal human melanocytes (HEMa-LP). The data shown in FIG. 1, panel A indicate that hnRNP A18 is not detected in normal melanocytes but is over expressed in four of the six cell lines studied as compared to normal melanocytes. hnRNP A18 expression levels does not seem to be dependent on a BRAF mutant genotype since all the melanoma cell lines shown in FIG. 1, part A harbor the BRAF mut/NRAS wild-type genotype and expressed different levels of hnRNP A18. Nonetheless, in order to verify whether hnRNP A18 levels are associated with BRAF or NRAS mutations we performed Western blot analysis with SK-MEL cell lines harboring different BRAF and NRAS genotypes. Data shown in FIG. 1, part B indicate that hnRNP A18 is also expressed in melanoma cells harboring the BRAF wild-type genotype regardless of NRAS status (SK-MEL-2: BRAF wild-type, NRAS mutant; SK-MEL-31: BRAF wild-type, NRAS wild-type). It thus appears that hnRNP A18 levels are not dependent on BRAF genotype.

Because hnRNP A18 can translocate from the nucleus to the cytosol in response to the hypoxia mimetic agent $CoCl_2$ (Yang et al., J Biol Chem. 2010; 285(12):8887-8893) and that fifty to sixty percent of locally advanced solid tumors, including melanoma, develop hypoxic areas, we next investigated whether hypoxic conditions could affect hnRNP A18 levels.

The data (FIG. 1, part C) indicate that hnRNP A18 levels increase following $CoCl_2$ exposure in melanoma but not in normal melanocytes (lanes 4 and 2). Down regulation of hnRNP A18 with shRNA abolished hnRNP A18 induction by $CoCl_2$ (lanes 5 and 6). We then measured the effect of hnRNP A18 expression on the cells' capacity to survive $CoCl_2$ exposure. The data shown in FIG. 1, part D indicate that down regulation of hnRNP A18 significantly increased LOX-IMVI sensitivity to $CoCl_2$, while re-expressing hnRNP A18 in cells that were stably transfected with shh-nRNP A18 (inset FIG. 1, part D) rescued $CoCl_2$ resistance at every dose tested (FIG. 1D). These data show for the first time that hnRNP A18 is over expressed in melanoma cells and that it could provide growth advantages to tumors.

hnRNP A18 confers a growth advantage to cancer cells in vivo.

To verify the functional significance of these findings, the effects of hnRNP A18 down regulation on tumor growth were evaluated in vivo. Melanoma LOX-IMVI cells stably transfected with shhnRNP A18 were injected in the left flanks of athymic mice (nu/nu) while LOX-IMVI cells stably transfected with a scrambled shRNA were injected in the right flanks of the same animals. The data shown in FIG. 2, parts A-B indicate that down regulation of hnRNP A18 significantly reduces melanoma tumor growth by about 50% and tumor weight by about 60% as compared to control (scrambled) tumors. Tumor progression (FIG. 2, part A) indicates that the difference between control (scrambled shRNA) and shhnRNP A18 tumors is more pronounced after the first week of tumor growth.

Because hnRNP A18 is translocated to the cytosol in response to hypoxic conditions (Yang et al., J Biol Chem. 2010; 285(12):8887-8893) and can regulate expression of stress-responsive transcripts, we next evaluated whether hnRNP A18 could affect the expression of HIF-1A, a key regulator of the cellular response to hypoxia. Data from tissue extracted from four tumors grown in vivo from cells expressing reduced (FIG. 2, part C, shA18, lanes 3, 4) or endogenous (sc, lanes 1, 2) hnRNP A18 levels indicate that down regulation of hnRNP A18 prevents up-regulation of HIF-1α in the tumors.

Figure 2:
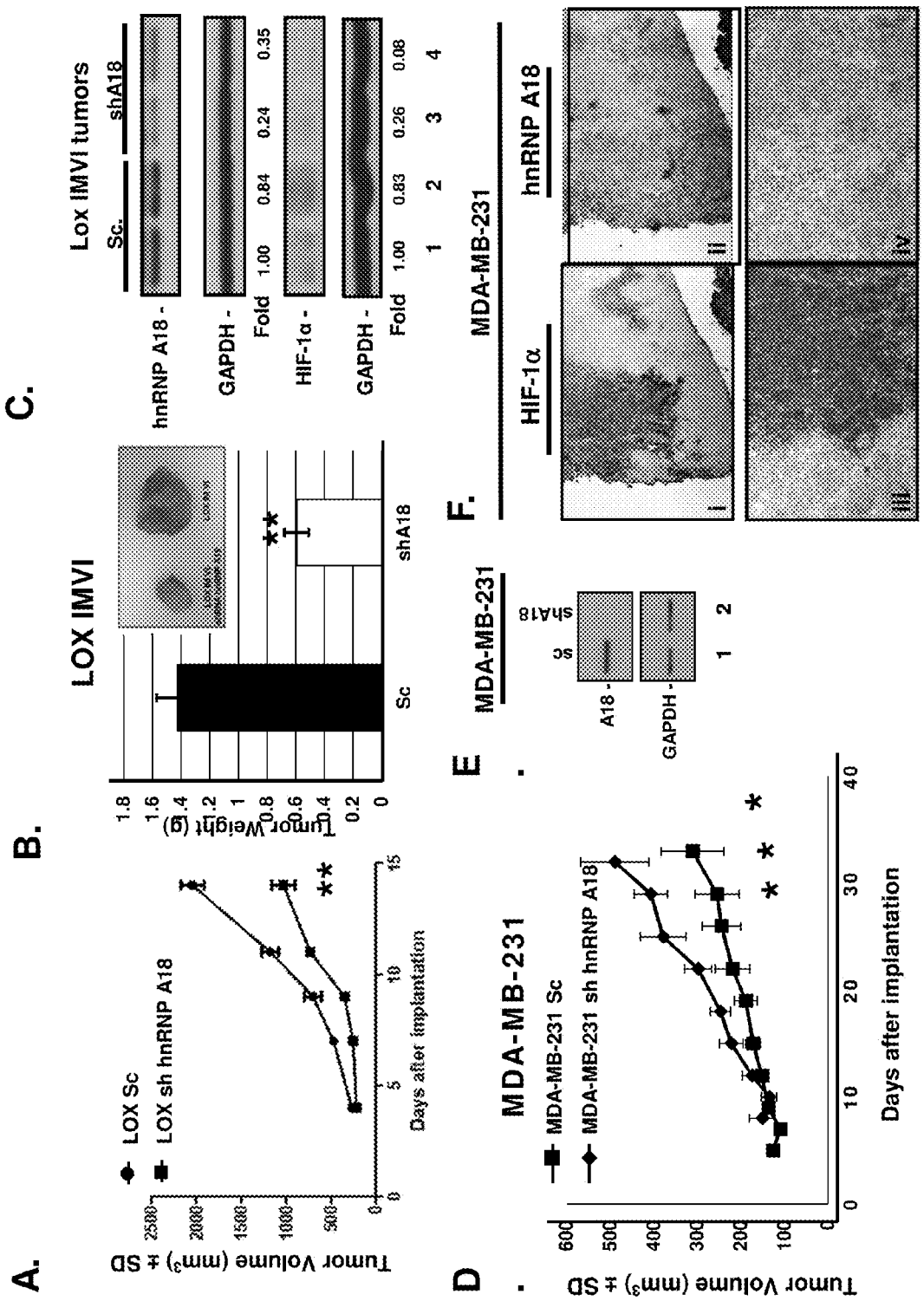
FIG. 2: hnRNP A18 promotes human tumor growth in vivo. Mouse Xenograft models: A) LOX-IMVI melanoma xenografts. LOX-IMVI cells stably transfected with either scrambled RNA or shhnRNP A18 were injected s.c. in the flanks of athymic mice (nu/nu). Tumor volumes were measured by caliper at the indicated intervals. B) Tumors were excised and weighed 12-15 days later. Average tumor weight from seven animals Black bar; tumor from LOX-IMVI stably transfected with scrambled RNA (sc), white bar; tumor from LOX-IMVI cells stably transfected with shhn-RNP A18. Inset: Left-hand side tumor formed with LOX-IMVI cells stably transfected with shhnRNP A18 injected on the left flank. Right-hand side, tumor formed in the same animal injected on the right-hand side with LOX-IMVI cells. C) Western blots analysis from tissue excised from tumors formed in vivo. Each lane indicates analysis performed on tissue extracted from same tumor with the indicated antibody. Fold induction was calculated by densitometry and normalized to GAPDH. D) Same as in A) except that breast MDA-MB-231 cells were used. E) Western blots performed on the indicated MDA-MB-231 cells before injections into the mice. F) Immunohistochemistry performed on a tumor formed in a mouse xenograft injected with MDA-MB-231 cells stably transfected with scrambled RNA. Two consecutive microtome sections from the same tumor were stained with either HIF-1α (i, iii) or hnRNP A18 (ii, iv) and counter stained with Mayer's Hematoxylin and mounted on coverslips. Magnification; 4× (i, ii) and 10× (iii, iv). $*p<0.05$, $**p<0.005$

To determine whether the effect of hnRNP A18 on tumor growth was cell type specific, a tumor progression experiment with breast cancer cells was performed. The data shown in FIG. 2, part D indicate that down regulation of hnRNP A18 significantly reduced breast cancer tumor growth as compared to tumors formed with MDA-MB-231 cells stably transfected with scrambled RNA (FIG. 2, part E). Moreover, immunohistochemistry staining of the breast cancer tumors formed in vivo indicate that hnRNP A18 accumulates in the hypoxic region of the tumor as defined by HIF-1α staining (FIG. 2, part F). These data thus suggest that over expression of hnRNP A18 in tumor cells promotes tumor growth.

hnRNP A18 promotes proliferation, invasion and migration.

Figure 3:
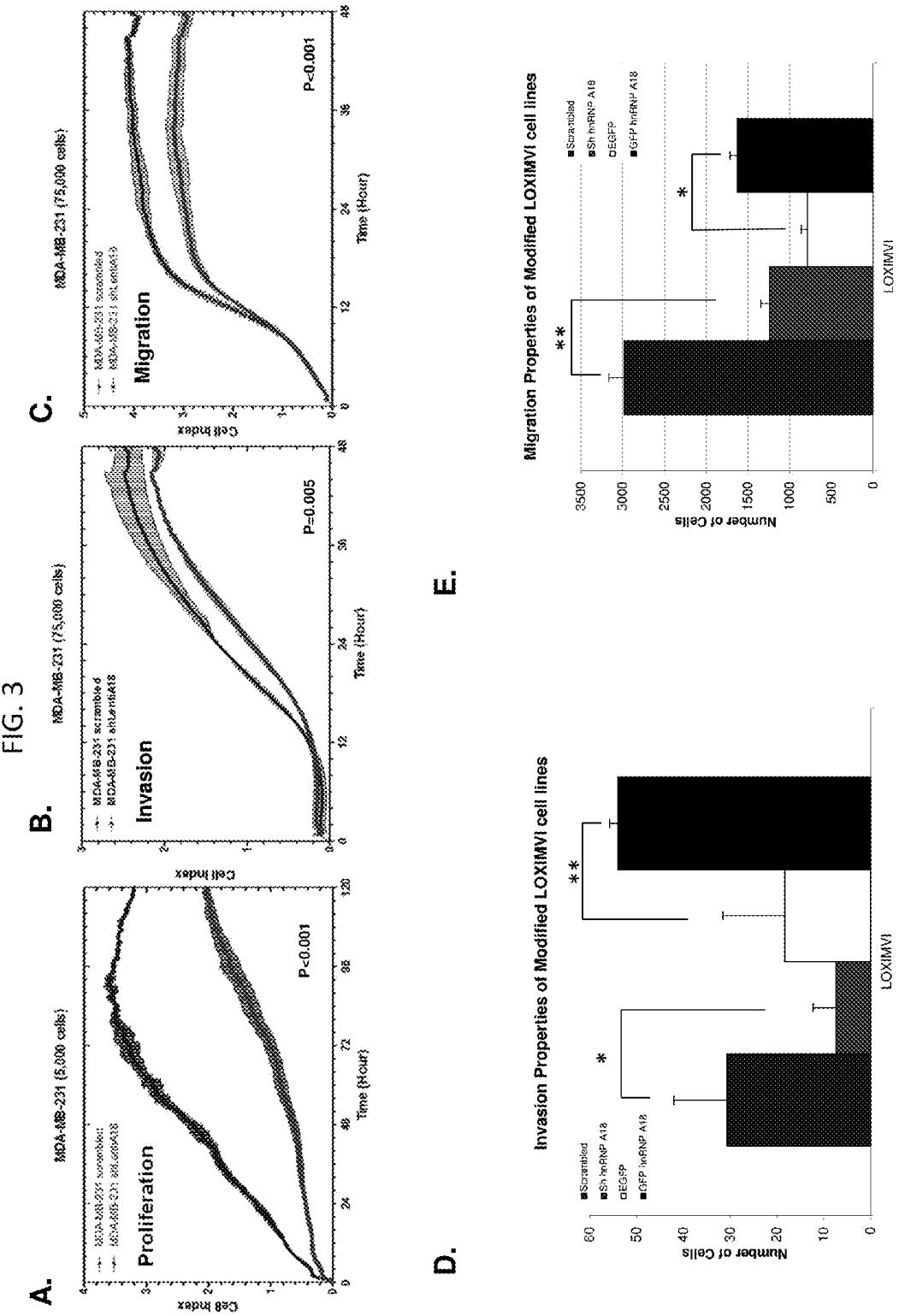
FIG. 3: hnRNP A18 increases proliferation, invasion and migration. A) Proliferation, B) Invasion and C) Migration assays performed on breast MDA-MB-231 cells stably transfected with shhnRNP A18 or scrambled RNA. Assays were performed on xCELLigence as described in the text. For all assays, events were measured by cell-sensor impedance, expressed as arbitrary unit Cell Index (CI), defined as (RnRb)/15, where Rn is the cell-electrode impedance of a cell-containing well and Rb is background impedance in wells containing only media. P values are as indicated. D) Invasion assay performed on melanoma LOX-IMVI cells stably transfected with shhnRNP A18, scrambled RNA, GFP-hnRNP A18 or EGFP. Assays were performed in Corning MATRIGEL Invasion chambers as described in the text. E) Migration assays performed as described in D) except that the assays were performed in Transwell Boyden chambers. $*p<0.05$, $**p<0.005$

To determine if hnRNP A18 over expression in human tumors could affect proliferation, invasion and/or migration, these parameters were monitored in real-time with an xCEL-Ligence RTCA MP instrument by measuring cell sensor impedance on cells expressing endogenous or reduced hnRNP A18 levels (shA18). The data shown in FIG. 3, parts A-C indicate that down regulation of hnRNP A18 significantly reduced breast cancer cells' proliferation, invasion and migration. Similar data were obtained by conventional invasion and migration assays performed with melanoma cells. The data shown in FIG. 3, parts D-E indicate that down regulation of hnRNP A18 significantly reduces melanoma cells' invasion and migration properties while over expression of hnRNP A18 significantly increases these parameters.

hnRNP A18-mediated growth advantages is mediated in part through HIF-1α regulation.

To determine whether hnRNP A18 could modulate HIF-1α levels and consequently cells' sensitivity to the hypoxic environment, it was evaluated whether hnRNP A18 could bind to the HIF-1α transcript. RNA immunoprecipitation was performed on polysomes extracted under conditions that preserved the association of RNA-binding proteins with target mRNA, essentially as described before (Yang et al., Nucleic Acids Res. 2006; 34(4):1224-1236; Tenenbaum et al., Methods. 2002; 26(2):191-198). hnRNP A18-bound mRNAs were then eluted and used for RT-PCR to amplify the products. The data shown in FIG. 4, part A indicate that hnRNP A18 does bind to HIF-1αmRNA in the absence and presence of $CoCl_2$. However, although the amount of HIF-1α mRNA pulled down by hnRNP A18 antibody in the presence of $CoCl_2$ (A18+$CoCl_2$) is apparently higher than in the absence of $CoCl_2$, the difference is not statistically significant. Nonetheless, hnRNP A18 could potentially affect HIF-1α transcript stability.

To verify this possibility, mRNA stability experiments were performed in the presence of Actinomycin D and reduced amounts of hnRNP A18. The data (FIG. 4, part B) indicate that in absence of $CoCl_2$, HIF-1α mRNA half-life is 2.06 h. Down regulation of hnRNP A18 reduces this half-life to 1.72 h for a 0.34 h difference. In the presence of $CoCl_2$, HIF-1α half-life increases to 3.26 h and down regulation of hnRNP A18 reduces it to 1.43 h for a difference of 1.83 h. Therefore, the data indicate that the binding of hnRNP A18 HIF-1α mRNA in the presence of $CoCl_2$ (FIG. 4, part A) significantly increases HIF-1αmRNA half-life by almost 2 h. It was next determined if the interaction of hnRNP A18 with HIF-1α mRNA is affecting HIF-1α protein levels. The data shown in FIG. 4C indicate that HIF-1α is over expressed in response to $CoCl_2$ (lanes 2 and 4) but down regulation of hnRNP A18 significantly reduces HIF-1α protein levels in response to $CoCl_2$ (lane 6 and FIG. 4, part D). Similar data were also obtained when cells were grown under hypoxia (0.5% O2) where down regulation of hnRNP A18 resulted in reduced HIF-1α protein expression levels (FIG. 4, part E). These data are in good agreement with FIG. 2, part F showing expression of hnRNP A18 in the hypoxic area of human tumors where HIF-1α is expressed and likely to be regulated by hnRNP A18.

hnRNP A18 affects angiogenesis factors.

Figure 5:
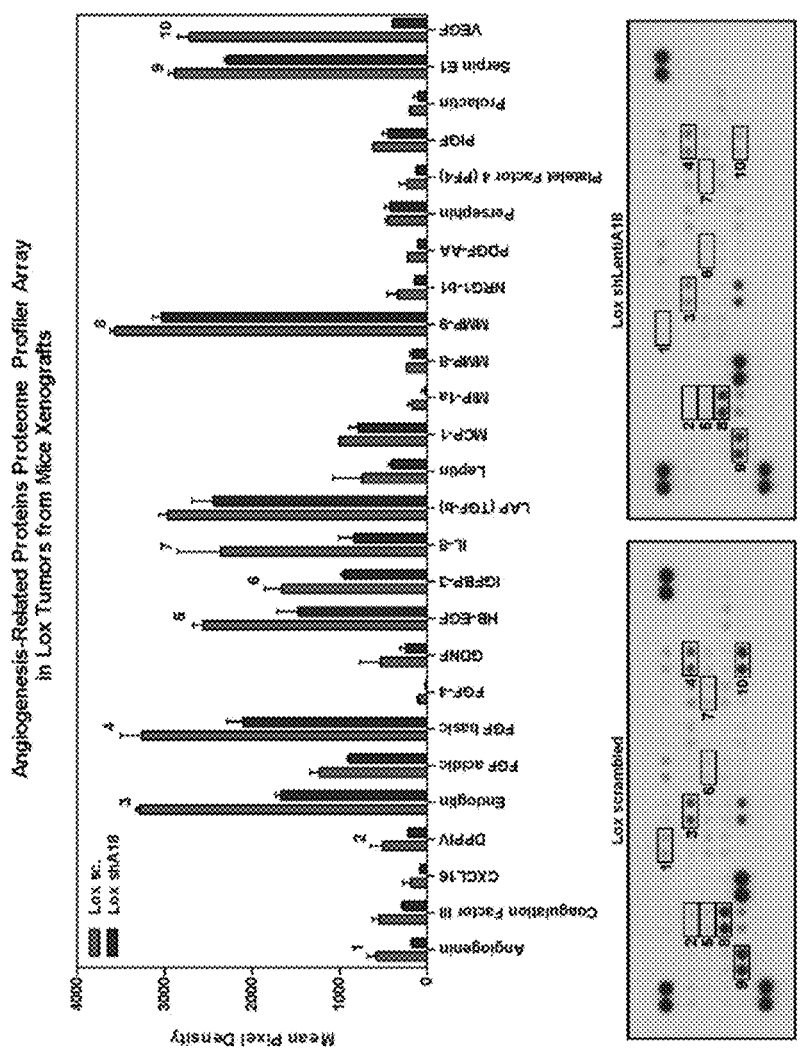
FIG. 5: Angiogenesis Proteome Profiler Array. Lox tumors expressing endogenous (sc; white bars) or reduced (sh; black bars) hnRNP A18 levels were excised from mouse xenografts, proteins extracted and analyzed as described in the text. Expression levels of angiogenesis proteins were measured by densitometry and expressed as mean pixel density after subtracting background.

One of the main contributions of HIF-1α to tumor promotion is the upregulation of angiogenic growth factors that provide oxygen to the hypoxic tumors (Dewhirst et al., Nat Rev Cancer. 2008; 8(6):425-437). To determine whether hnRNP A18 could affect HIF-1α functions in growing tumors in vivo the angiogenic proteomes of melanoma tumors expressing endogenous or reduced hnRNP A18 levels were evaluated. Of the fifty-five angiogenic factors evaluated, about half including angiogenin, endoglin and most specifically VEGF (FIG. 5, box 10), a prime HIF-1α regulated growth factor, were down regulated in the shhnRNP A18 tumor as compared to control. These data are in good agreement with the in vivo data (FIG. 2) indicating that down regulation of hnRNP A18 prevent tumor growth.

Figure 11:
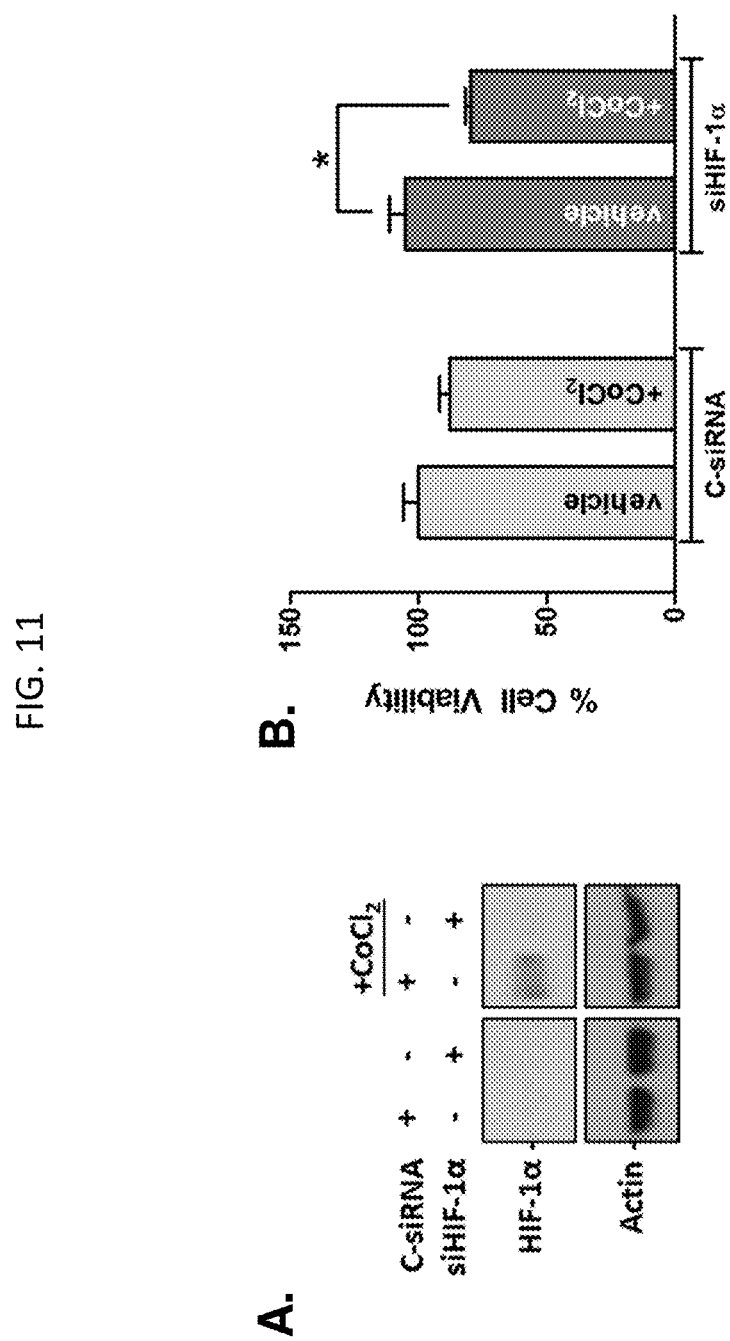
FIG. 11: Down regulation of HIF-1α reduces cell viability in the presence of $CoCl_2$. A) Western blot analysis of LOX-IMVI cells transiently transfected with scrambled siRNA (control, C-siRNA) or HIF-1 α siRNA (siHIF-1α) and treated (+) or not (−) with 50 μM $CoCl_2$. The blots were hybridized with the indicated antibodies. B) Cell viability performed on LOX-IMVI cells transiently transfected with scrambled siRNA (control, C-siRNA) or HIF-1 α siRNA (siHIF-1 α) and treated (+) or (−) with 50 μM $CoCl_2$. WST-1 assays were performed as indicated in Material and Methods and viability is expressed as a percentage of the respective untreated samples. *=$p<0.05$

To further confirm that HIF-1α could contribute to hnRNP A18 growth promoting activity, HIF-1α was down regulated in melanoma cells and measured cell viability in the presence of $CoCl_2$. The data (FIG. 11) indicate that indeed down regulation of HIF-1α significantly reduces cell viability in the presence of $CoCl_2$.

hnRNP A18 RNA binding signature motif in cancer promoting genes.

Figure 6:
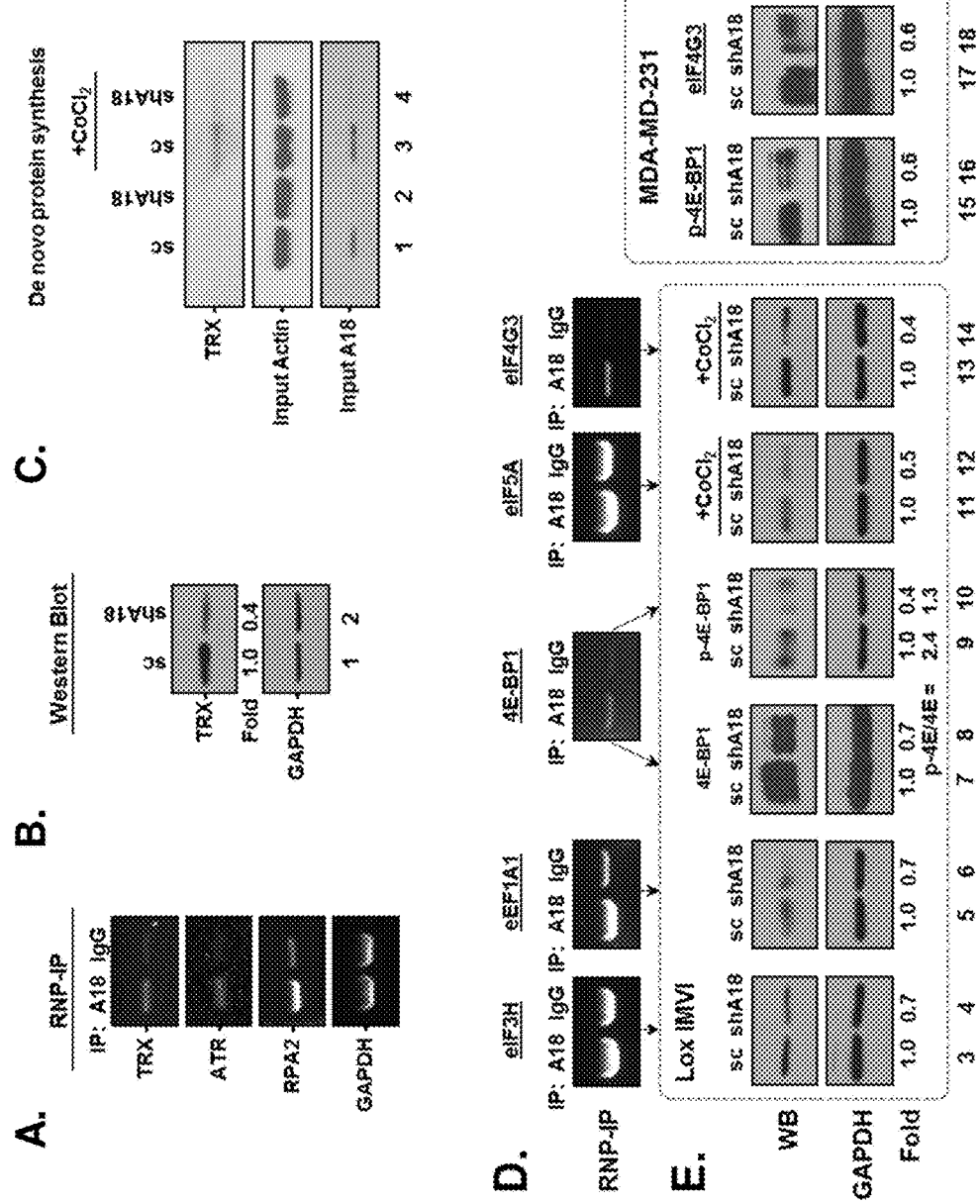
FIG. 6: hnRNP A18 targeted transcripts. A) and D) RNA bound to Ribonucleoprotein was immunoprecipitated (RNP-IP) from LOX-IMVI cells with the indicated antibody. GAPDH was amplified from the same fractions to confirm that equal amounts of mRNA were present in each immunoprecipitated sample. B) Western blot analysis performed in LOX-IMVI cells stably transfected with scrambled (sc) or shhnRNP A18 RNA (shA18) with the indicated antibodies. Fold induction was calculated by densitometry and normalized to GAPDH. C) De novo protein synthesis. LOX-IMVI cells stably transfected with scrambled (lanes 1, 3) or shhnRNP A18 RNA (lanes 2, 4) were exposed (lanes 3, 4) or not (lanes 1, 2) to $CoCl_2$ in methionine-free media and labeled with Click-iT® Metabolic Labeling Reagents as described in the text. TRX antibody was incubated with the newly biotinylated protein and detected by chemiluminescent with anti-Streptavidin-HRP antibody. Actin was used as loading control. E) Western blot analysis performed as in B) in LOX-IMVI cells (lanes 1-12) and MDA-MB-231 cells (lanes 13-16) with the indicated antibodies. Fold induction was calculated by densitometry and normalized to GAPDH. Ratio of p-4E-BP1 over 4E-BP1 was calculated by densitometry (lanes 5-8) normalized to GAPDH.

The hnRNP A18 RNA binding signature motif has been identified and validated in a number of transcripts associated with tumor progression (Yang et al., Nucleic Acids Res. 2006; 34(4):1224-1236; Yang et al., J Biol Chem. 2010; 285(12):8887-8893). As with most key regulatory proteins mediating survival benefits, we expect that the transcripts targeted by hnRNP A18 will mediate different cellular functions that will result in an overall growth advantage to the tumor when coordinately upregulated. A search of the UniGene database revealed that indeed the hnRNP A18 RNA signature motif could be located in the 3' UTRs of transcripts associated with proliferation, survival and invasion (FIG. 12). ATR, RPA2 and TRX have been validated before as hnRNP A18 targets in colon cancer cells (Yang C and Carrier F., J Biol Chem. 2001; 276(50):47277-47284; Yang et al., Nucleic Acids Res. 2006; 34(4):1224-1236; Yang et al., J Biol Chem. 2010; 285(12):8887-8893) and are used here as positive controls for hnRNP A18 binding to targeted transcripts in melanoma cells. The data shown in FIG. 6, part A indicate that TRX transcript is pulled down by hnRNP A18 antibody but not the nonspecific IgG antibody in melanoma cells. Western blot analyses indicate that down regulation of hnRNP A18 reduced the basal protein levels of TRX in melanoma cells (FIG. 6, part B). Because hnRNP A18 is associated with low molecular weight polysomes (Yang et al., Nucleic Acids Res. 2006; 34(4):1224-1236), we next wanted to evaluate the effect of hnRNP A18 on newly synthesized proteins. The data shown in FIG. 6, part C indicate that down regulation of hnRNP A18 prevents the accumulation of newly synthesized TRX protein in the presence of the hypoxia mimetic agent $CoCl_2$ (lane 3-4). These data thus support the notion that hnRNP A18 increases mRNA stability (FIG. 4B) and translation of its targeted transcripts under cellular stress conditions.

A search of the UniGene database also identified several members of the general translational machinery as potential hnRNP A18 targets (FIG. 12). RNP-IP performed with hnRNP A18 antibody validated this prediction and indicated that indeed hnRNP A18 could efficiently bind to eIF3H, eEF1A1, eIF4E-BP1, eIF5A and eIF4G3 (FIG. 6, part D). Western blot analyses indicate that down regulation of hnRNP A18 reduced the basal protein levels of its targeted transcripts in melanoma and breast cancer cells (FIG. 6, part E). Of particular interest is the effect of hnRNP A18 down regulation on eIF4E-BP1. When phosphorylated, eIF4E-BP1 relieves the translational repression imposed on eIF4E and allows translation to proceed. By regulating eIF4E-BP1 levels, hnRNP A18 also affects the levels of phosphorylated eIF4E-BP1 (p-eIF4E-BP1, FIG. 6, part E, lanes 7-8) and could affect translation. In fact, the ratio of p-eIF4E-BP1 over total eIF4E-BP1 decreases by almost 50% in cells expressing reduced hnRNP A18 levels (FIG. 6, part E, lanes 5-8). In order to determine if the regulatory function of hnRNP A18 under cellular stress was specific to TRX and HIF-1α the protein levels of eIF4G3 and eIF5A in the presence of $CoCl_2$ was also evaluated. The data indicate that down regulation of hnRNP A18 reduces the protein levels of these two transcripts in the presence of $CoCl_2$ (FIG. 6, part E, lanes 9-12).

hnRNP A18 is over expressed in human tumors including melanomas.

hnRNP A18 (CIRP) levels are elevated in several human tumors, but it is believed that hnRNP A18 levels in primary melanoma and correlation to tumor grades have not yet been investigated (Artero-Castro et al., Mol Cell Biol. 2009; 29(7):1855-1868). In order to evaluate the potential clinical significance of hnRNP A18 upregulation, immunohistochemistry was performed on tissue microarrays (TMA) from 295 human samples including 70 primary and metastatic melanoma samples (Table 1).

TABLE 1 hnRNP A18 protein expression in human cancer as evaluated by immunohistochemistry on Tissue Micro arrays (TMAs).

| | Staining scores | | | | % Location | | | | Total |
|---|---|---|---|---|---|---|---|---|---|
| Cancer Type | % Negative | % Weak | % Moderate | % Strong/Very strong | N | N/C | C/N | C | No of patients |
| Melanoma | | | | | | | | | |
| Normal skin | 43 | 14 | 14 | 29 | 100 | | | | 7 |
| Primary | 4 | 12 | 42 | 42 | 13 | 26 | 39 | 22 | 46 |
| Metastatic | 42 | | 16 | 42 | 57 | 43 | | | 24 |
| Lymph Node | | | | | | | | | |
| Prostate | | | | | | | | | |
| Hyperplasia | 0 | 0 | 80 | 20 | 80 | 20 | | | 10 |
| Adenocarcinoma | 0 | 0 | 36 | 64 | 64 | 36 | | | 28 |
| Metastatic rectum | 0 | 100 | 0 | 0 | 100 | | | | 2 |
| Breast | | | | | | | | | |
| Ductal carcinoma In situ | 0 | 17 | 50 | 33 | 50 | 50 | | | 6 |
| Invasive Ductal carcinoma | 12 | 15 | 33 | 40 | 24 | 75 | | | 77 |
| Invasive lobular carcinoma | 0 | 0 | 50 | 50 | 43 | 57 | | | 8 |

TABLE 1-continued hnRNP A18 protein expression in human cancer as evaluated by immunohistochemistry on Tissue Micro arrays (TMAs).

| Cancer Type | Staining scores | | | | % Location | | | | Total No of patients |
|---|---|---|---|---|---|---|---|---|---|
| | % Negative | % Weak | % Moderate | % Strong/Very strong | N | N/C | C/N | C | |
| Colon | | | | | | | | | |
| Normal colon | 50 | 50 | 0 | 0 | 100 | | | | 2 |
| Malignant Grade I | 25 | 25 | 25 | 25 | 50 | 50 | | | 4 |
| Malignant grade I-II | 22 | 15 | 26 | 37 | 48 | 22 | | 3 | 27 |
| Malignant Grade II | 21 | 18 | 34 | 27 | 87 | 13 | | | 33 |
| Malignant Grade II-III | 40 | 10 | 10 | 40 | 10 | 30 | 10 | | 10 |
| Malignant Grade III | 27 | 36 | 28 | 9 | 100 | | | | 11 |
| Total | | | | | | | | | 295 |

Figure 7:
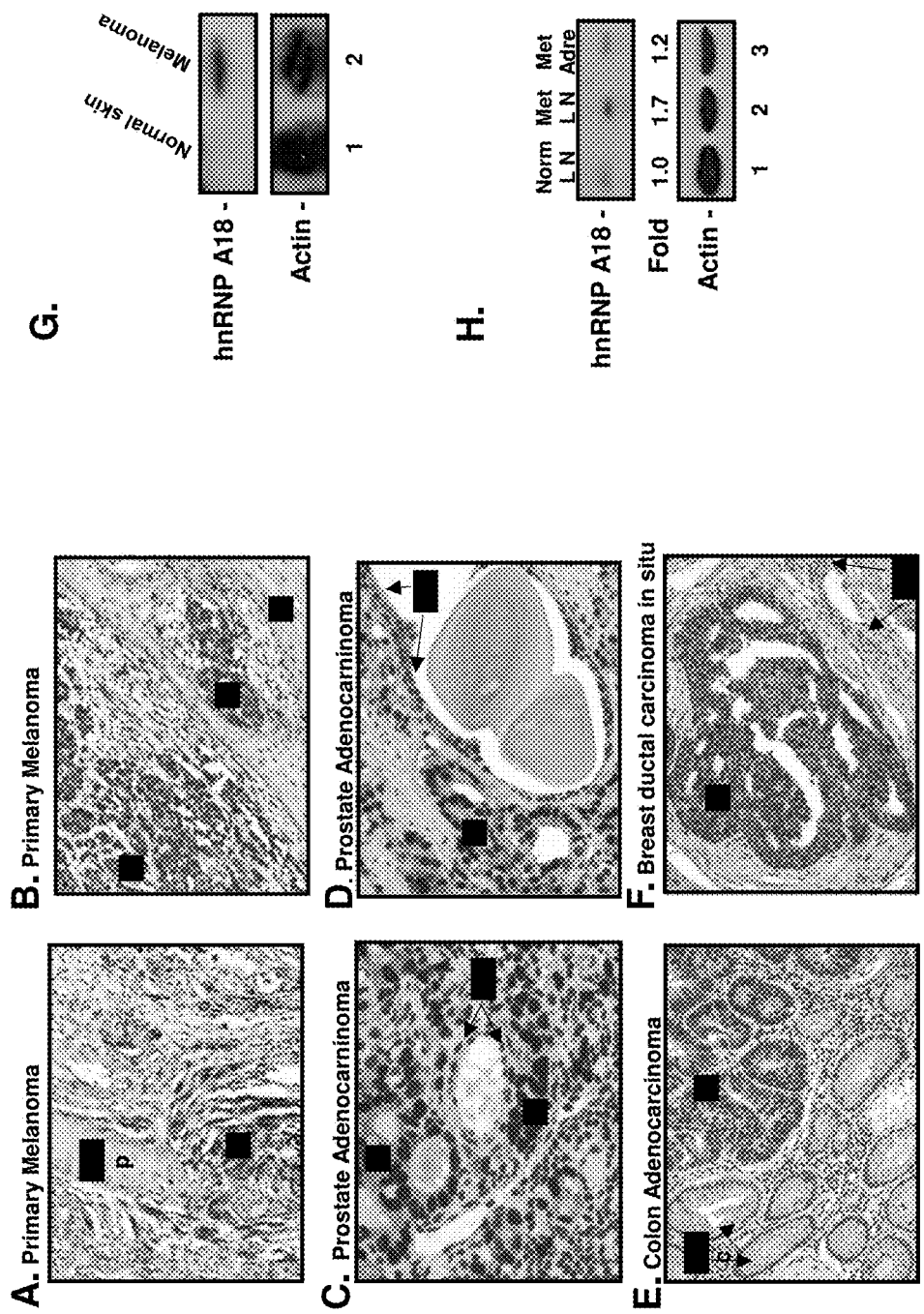
FIG. 7: hnRNP A18 expression in human tumors. Tissue microarrays (TMA). A)-B) Immunohistochemistry of primary melanoma with built-in adjacent normal skin. A) Stained tumor cells (t) near negative dermal papillae (dp). B) Tumor cells (t), including tumor cells in the derma (dt) were strongly positive for hnRNP A18 while adjacent normal skin (d) showed no or very weak staining. C-D) Prostate adenocarcinoma shows strong nuclear staining in the tumor cells (t) while adjacent normal prostate (np) showed no or very weak staining. E) Colon adenocarcinoma with built-in adjacent normal colon shows strong nuclear hnRNP A18 staining in the tumor cells (t) but weak staining in the adjacent normal colon (nc) where well defined lobular pattern of colonic crypts divided by smooth muscle bundles can be observed. F) A ductal carcinoma in situ shows strong hnRNP A18 nuclear staining in tumor cells (t) while adjacent normal breast (nb) showed no or very weak staining. G-H) Western blots from human tissues. G) Proteins were extracted from normal skin or melanoma skin tumors and analyzed by Western blots with the indicated antibodies. H) Same as G) except that the proteins were extracted from normal lymph nodes (Norm LN) or metastatic melanoma tumors to the lymph nodes (Met LN) or the adrenals (Met Adre). Fold induction was calculated by densitometry and normalized to Actin.
Figure 8:
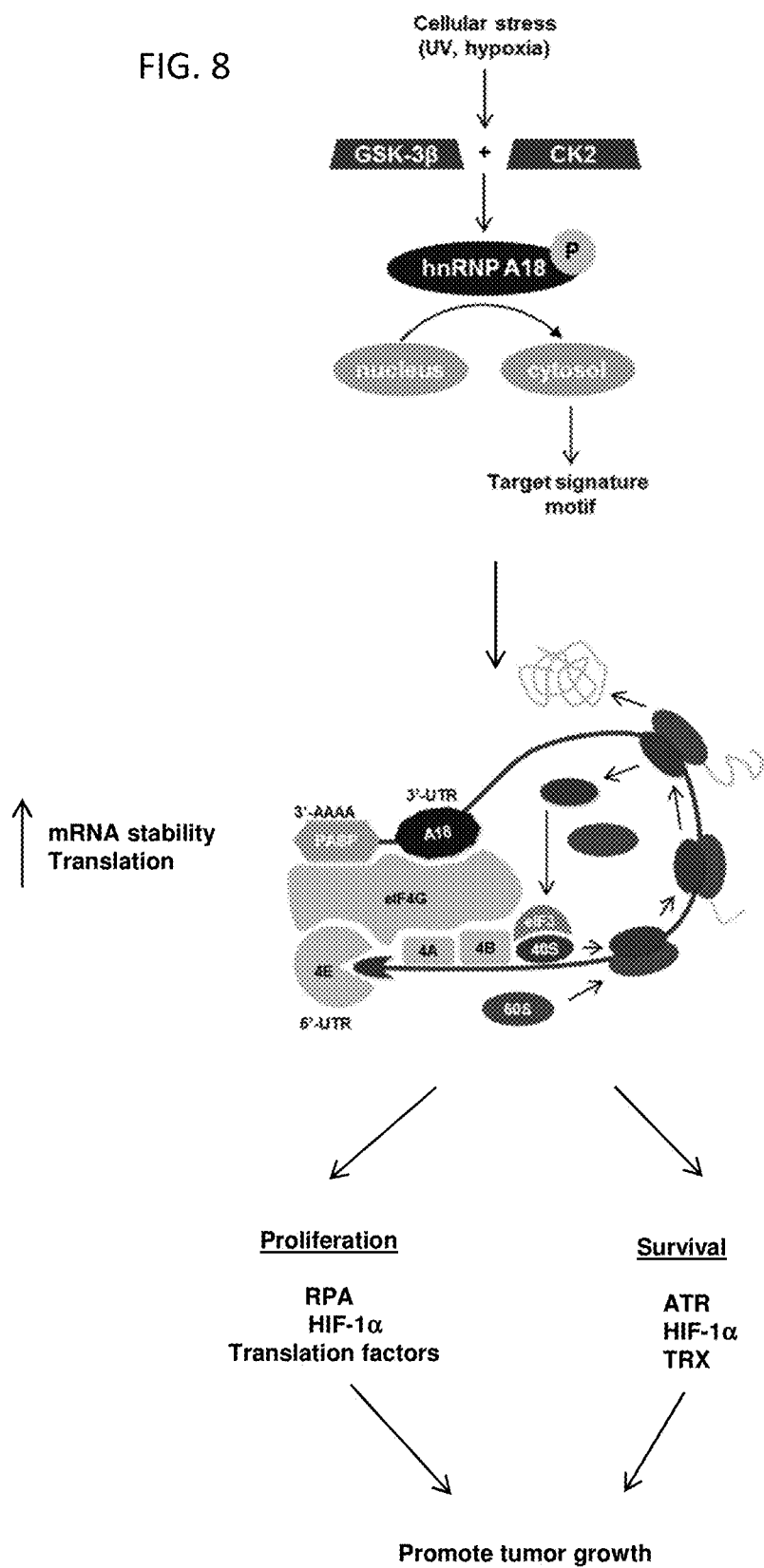
FIG. 8: Without being bound by theory, a proposed mechanism for hnRNP A18 tumor promoting activity. In response to cellular stress such as UV radiation and hypoxia, the predominantly nuclear hnRNP A18 is phosphorylated by GSK-3β and CK2 and translocates to the cytosol (Yang C and Carrier F., J Biol Chem. 2001; 276(50):47277-472845; Yang et al., J Biol Chem. 2010; 285(12):8887-8893.). In the cytosol, hnRNP A18 recognizes a specific signature motif in the 3'UTR of the targeted transcripts and increases their translation by associating with eIF4G on polysomes (Yang et al., Nucleic Acids Res. 2006; 34(4):1224-1236; Yang et al., J Biol Chem. 2010; 285(12):8887-8893). In response to cellular stress, hnRNP A18 up-regulates the translation of transcripts conferring tumor growth advantages such as HIF-1α, RPA, TRX, ATR and components of the general translational machinery. PABP: PolyA Binding Protein. The arrows on the right panel indicate the direction of ribosome scanning and translating.
Figure 9:
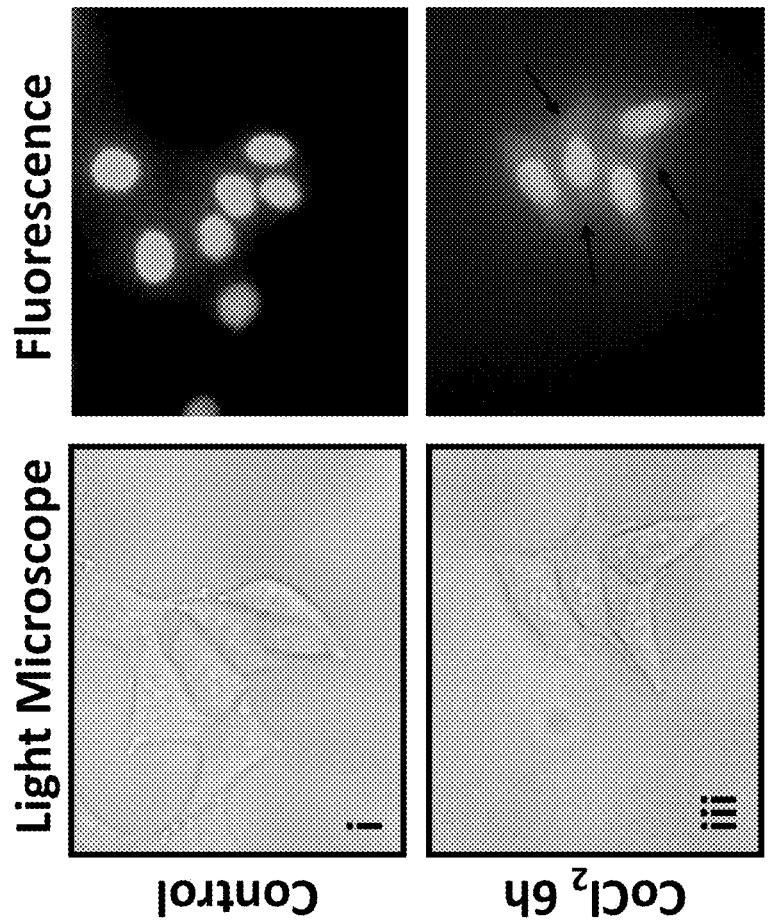
FIG. 9: Nuclear to cytoplasmic translocation of hnRNP A18 after CoCl2. RKO cells were treated with CoCl2 for 6 h and imaged for hnRNP A18-GFP under light microscope (i and iii) or fluorescence (ii and iv). hnRNP A18-GFP can be seen in the cytoplasm after CoCl2 treatment (iv) compared to control (ii).
Figure 10:
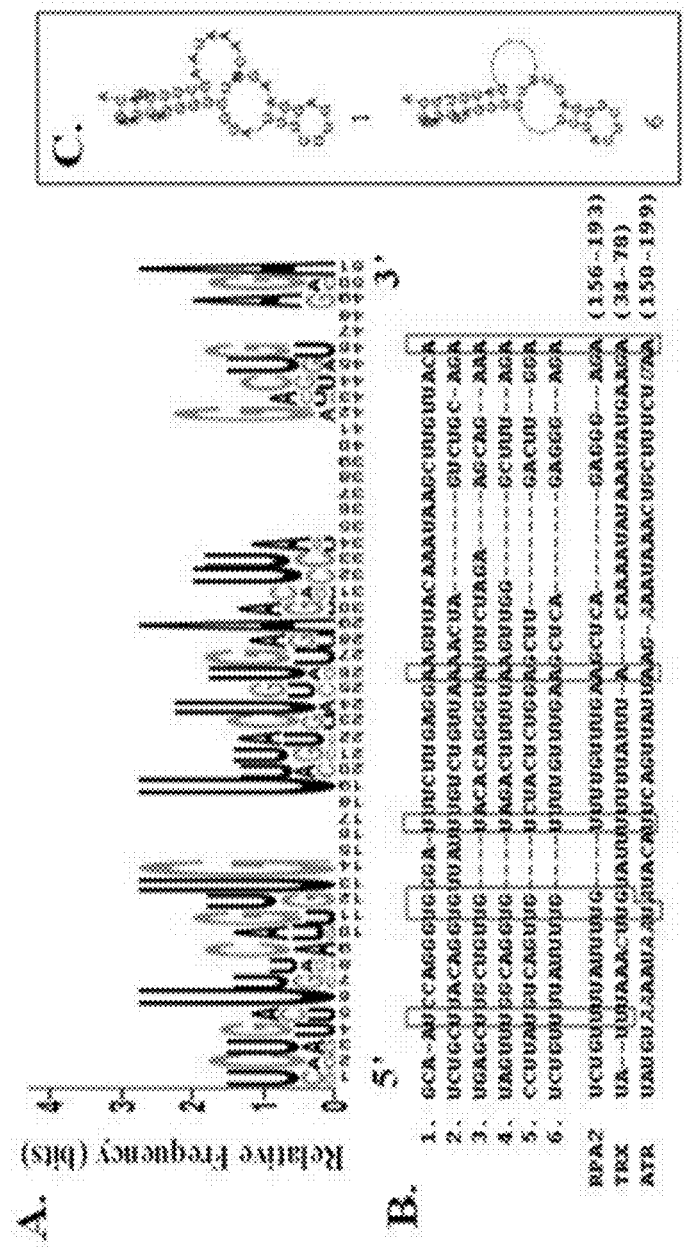
FIG. 10: A) Probability matrix representing relative frequency of each residue in hnRNP A18 targets B) Sequence alignment of hnRNP A18 putative motif C) Predicted secondary structure of version 1 and 6 hnRNP A18 putative motif.

Among primary melanomas, 42% showed moderate staining and 42% showed strong/very strong staining, while adjacent normal skin showed no or very weak staining Representative staining patterns are shown in FIG. 7 where stained primary melanoma tumor cells near negative dermal papilla (FIG. 7, part A) and tumor cells in the derma (FIG. 7, part B) were strongly positive for hnRNP A18, while adjacent normal skin showed no or weak staining. In metastatic melanoma cases, 58% showed moderate to strong staining while 42% were negative. Comparable patterns of expression were also observed in colon, prostate, and breast cancer TMA samples (FIG. 7, parts A-F, Table 1) where higher hnRNP A18 expression was observed in the cancer cells as compared to normal adjacent tissue. Although no apparent correlation with tumor grades was observed in colon cancer, stronger hnRNP A18 staining was observed in more advanced prostate and breast cancers as compared to non-cancer prostate (prostate hyperplasia) and noninvasive breast cancer tissues (ductal carcinoma in situ) (Table 1). While hnRNP A18 is predominantly a nuclear protein, staining was exclusively cytoplasmic in 20% of malignant melanomas and always nuclear in normal cells. This is consistent with the capacity of hnRNP A18 to translocate to the cytosol in response to cellular stress such as UV radiation and hypoxia. These immunohistochemistry data are in good agreement with the levels of hnRNP A18 protein as measured by Western blots in human melanoma tumor tissues (FIG. 7, parts G-H). hnRNP A18 protein levels were found to be elevated in primary melanoma as compared to normal skin tissue and slightly more elevated in melanoma which metastasized to the lymph nodes as compared to protein extracted from normal lymph nodes (FIG. 7, parts G-H).

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein. All patents and publications mentioned and/or cited herein are incorporated by reference to the same extent as if each individual publication was specifically and individually indicated as having been incorporated by reference in its entirety.

What is claimed is:

1. A method of treating cancer in a subject with cancer, wherein the cancer has increased expression of heterogenous ribonucleoprotein A18 (hnRNP A18) relative to control cells, consisting essentially of administering to the subject a therapeutically effective amount of a composition that decreases the level and/or activity of heterogenous ribonucleoprotein A18 (hnRNP A18), wherein the composition consists essentially of a nucleic acid molecule that comprises a nucleotide sequence that binds to at least a portion of a nucleotide sequence of hnRNP A18, wherein the cancer is selected from the group consisting of melanoma and breast cancer, wherein the subject is not administered one or more anti-cancer agents and/or radiotherapy in combination with the nucleotide sequence that binds to at least a portion of the nucleotide sequence of hnRNP A18.

2. The method of claim 1, wherein the nucleotide sequence of hnRNP A18 is SEQ ID NO: 1.

3. The method of claim 1, wherein a portion of the nucleic acid molecule is at least 70%, 75%, 80%, 85%, 90%, 91%, 92%, 93%, 94%, 95%, 96% 97%, 97%, 98% or 99% complementary to at least a portion of SEQ ID NO:1.

4. The method of claim 1, wherein the composition comprises a DNA molecule or an RNA molecule.

5. The method of claim 4, wherein the composition comprises an anti-sense DNA molecule or an anti-sense RNA molecule.

6. The method of claim 4, wherein the composition comprises a small interfering RNA (siRNA) molecule.

7. The method of claim 6, wherein the siRNA molecule comprises a double stranded molecule comprising SEQ ID NO:11 and SEQ ID NO:12.

8. The method of claim 1, wherein the composition comprises a small hairpin RNA (shRNA) molecule.

9. The method of claim 8, wherein the composition comprises an expression vector comprising SEQ ID NO: 3, SEQ ID NO: 4, SEQ ID NO: 5 or SEQ ID NO: 6.

10. The method of claim 9, wherein the expression vector is a lentivirus vector.

11. The method of claim 1, wherein the nucleic acid further comprises an expression vector.

12. The method of claim 11, wherein the expression vector is a viral vector or a non-viral vector.

13. The method of claim 12, wherein the viral vector is an adenoviral vector, an adeno-associated viral vector, a lentiviral vector, or a retroviral vector.

14. The method of claim 1, wherein the cancer comprises cancer tissue under hypoxic conditions.

15. The method of claim 1, wherein the method decreases tumor growth, proliferation, and/or survival of the cancer.

* * * * *

SEQUENCE LISTING

```
<160> NUMBER OF SEQ ID NOS: 22

<210> SEQ ID NO 1
<211> LENGTH: 1322
<212> TYPE: DNA
<213> ORGANISM: Homo sapiens

<400> SEQUENCE: 1
tagcttggca cgaggctcgg gtcgttgtgg tgcgctgtct tcccgcttgc gtcagggacc      60
tgcccgactc agtggccgcc atggcatcag atgaaggcaa acttttttgtt ggagggctga     120 gttttgacac caatgagcag tcgctggagc aggtcttctc aaagtacgga cagatctctg     180
aagtggtggt tgtgaaagac agggagaccc agagatctcg gggatttggg tttgtcacct     240
ttgagaacat tgacgacgct aaggatgcca tgatggccat gaatgggaag tctgtagatg     300
```

-continued

| | |
|---|---|
| gacggcagat ccgagtagac caggcaggca agtcgtcaga caaccgatcc cgtgggtacc | 360 |
| gtggtggctc tgccggggc cggggcttct tccgtggggg ccgaggacgg ggccgtgggt | 420 |
| tctctagagg aggaggggac cgaggctatg gggggaaccg gttcgagtcc aggagtgggg | 480 |
| gctacggagg ctccagagac tactatagca gccggagtca gagtggtggc tacagtgacc | 540 |
| ggagctcggg cgggtcctac agagacagtt acgacagtta cgctacacac aacgagtaaa | 600 |
| aaccctccct gctcaagatc gtccttccaa tggctgtgtg tttaaagatt gtgggagctt | 660 |
| cgctgaacgt taatgtgtag taaatgcacc tccttgtatt cccactttcg tagtcatttc | 720 |
| ggttctgatc ttgtcaaacc cagcctgacc gcttctgacg ccgggatggc ctcgttacta | 780 |
| gacttttctt tttaaggaag tgctgttttt ttttgagggt tttcaaaaca ttttgaaaag | 840 |
| catttacttt tttgaccacg agccatgagt tttcaaaaaa atcggggtt gtgtgggttt | 900 |
| ttggtttttg ttttagtttt tggttgcgtt gccttttttt tttagtgggg ttggccccat | 960 |
| gaagtgggtg ccccactcac ttctctgaga tcgaacggac tgtgaatccg ctctttgtcg | 1020 |
| gaagctgagc aagctgtggc ttttttccaa ctccgtgtga cgtttctgag tgtagtgtgg | 1080 |
| taggacccgg cgggtgtgca gcaactgccc tggagcccca cccctgcgt ccatctgtgc | 1140 |
| tgtgcgcccc acagtagacg tgcagacgtc cctgagaggt tcttgaagat gtttatttat | 1200 |
| attgtccttt tttactggaa gacgtacgca tactccatcg atgttgtatt tgcagtggct | 1260 |
| gaggaattct tgtacgcagt tttctttggc tttacgagcc gattaaaaga ccgtgtgaaa | 1320 |
| tg | 1322 |

<210> SEQ ID NO 2
<211> LENGTH: 19
<212> TYPE: DNA
<213> ORGANISM: Homo sapiens

<400> SEQUENCE: 2

| gagacagtta cgacagtta | 19 |
|---|---|

<210> SEQ ID NO 3
<211> LENGTH: 29
<212> TYPE: DNA
<213> ORGANISM: Homo sapiens

<400> SEQUENCE: 3

| gagaacattg acgacgctaa ggatgccat | 29 |
|---|---|

<210> SEQ ID NO 4
<211> LENGTH: 29
<212> TYPE: DNA
<213> ORGANISM: Homo sapiens

<400> SEQUENCE: 4

| tacgacagtt acgctacaca caacgagta | 29 |
|---|---|

<210> SEQ ID NO 5
<211> LENGTH: 29
<212> TYPE: DNA
<213> ORGANISM: Homo sapiens

<400> SEQUENCE: 5

| gatggacggc agatccgagt agaccaggc | 29 |
|---|---|

<210> SEQ ID NO 6
<211> LENGTH: 29

```
<212> TYPE: DNA
<213> ORGANISM: Homo sapiens

<400> SEQUENCE: 6
cggagtcaga gtggtggcta cagtgaccg                                    29

<210> SEQ ID NO 7
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 7
aacccattcc tcacccatca                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic construct; primer

<400> SEQUENCE: 8
tccacctctt ttggcaagca                                              20

<210> SEQ ID NO 9
<211> LENGTH: 24
<212> TYPE: DNA
<213> ORGANISM: Artificial sequence
<220> FEATURE:
<223> OTHER INFORMATION: Synthetic construct; primer

<400> SEQUENCE: 9
acatcaagaa ggtggtgaag cagg                                         24

<210> SEQ ID NO 10
<211> LENGTH: 25
<212> TYPE: DNA
<213> ORGANISM: Artificial sequence
<220> FEATURE:
<223> OTHER INFORMATION: Synthetic construct; primer

<400> SEQUENCE: 10
ccagcaagga tactgagagc aagag                                        25

<210> SEQ ID NO 11
<211> LENGTH: 21
<212> TYPE: RNA
<213> ORGANISM: Artificial sequence
<220> FEATURE:
<223> OTHER INFORMATION: synthetic construct

<400> SEQUENCE: 11
gagacaguua cgacaguuat t                                            21

<210> SEQ ID NO 12
<211> LENGTH: 21
<212> TYPE: RNA
<213> ORGANISM: Artificial sequence
<220> FEATURE:
<223> OTHER INFORMATION: synthetic construct

<400> SEQUENCE: 12
uaacugucgu aacugucuct t                                            21
```

```
<210> SEQ ID NO 13
<211> LENGTH: 47
<212> TYPE: DNA
<213> ORGANISM: Homo sapiens

<400> SEQUENCE: 13
ttaaaacttg taatttttttt aatttacaaa aatataaaat atgaaga            47

<210> SEQ ID NO 14
<211> LENGTH: 48
<212> TYPE: DNA
<213> ORGANISM: Homo sapiens

<400> SEQUENCE: 14
tccatatatg tgaaatgaaa ttatgtaaaa gaatatgtta ataatcta            48

<210> SEQ ID NO 15
<211> LENGTH: 43
<212> TYPE: DNA
<213> ORGANISM: Homo sapiens

<400> SEQUENCE: 15
tactcttgaa atctttagag caactttaag gcttgtaaat aca                 43

<210> SEQ ID NO 16
<211> LENGTH: 46
<212> TYPE: DNA
<213> ORGANISM: Homo sapiens

<400> SEQUENCE: 16
tcccagggtg gcggtggtgg cagcagtgat cctctgaacc tgcaga              46

<210> SEQ ID NO 17
<211> LENGTH: 45
<212> TYPE: DNA
<213> ORGANISM: Homo sapiens

<400> SEQUENCE: 17
ttttagtgtg gtttattgag ttcagcagtt ctcatattct gttta               45

<210> SEQ ID NO 18
<211> LENGTH: 47
<212> TYPE: DNA
<213> ORGANISM: Homo sapiens

<400> SEQUENCE: 18
tcagaactgt ttgtttcaat tggccattta agtttagtag taaaaga             47

<210> SEQ ID NO 19
<211> LENGTH: 46
<212> TYPE: DNA
<213> ORGANISM: Homo sapiens

<400> SEQUENCE: 19
tgtctagtgt tgtcttcatc aagaacagac tatatactaa ttccca              46

<210> SEQ ID NO 20
<211> LENGTH: 45
<212> TYPE: DNA
<213> ORGANISM: Homo sapiens

<400> SEQUENCE: 20
tccagggtgg gatttcttga ggaagttaca aataagcttg ttaca               45
```

```
<210> SEQ ID NO 21
<211> LENGTH: 42
<212> TYPE: DNA
<213> ORGANISM: Homo sapiens

<400> SEQUENCE: 21
tgaactcttg aagtcacacc agggcaactc ttggaagaaa ta                    42

<210> SEQ ID NO 22
<211> LENGTH: 43
<212> TYPE: DNA
<213> ORGANISM: Homo sapiens

<400> SEQUENCE: 22
taggttgatg tgcttgggaa agctccctcc ccctccttcc cca                   43
```